US007652037B2

(12) United States Patent
Rahbar et al.

(10) Patent No.: US 7,652,037 B2
(45) Date of Patent: *Jan. 26, 2010

(54) METHODS OF LOWERING LIPID LEVELS IN A MAMMAL

(75) Inventors: Samuel Rahbar, Beverly Hills, CA (US); James L. Figarola, Hacienda Heights, CA (US)

(73) Assignee: City Of Hope, Duarte, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 11/948,574

(22) Filed: Nov. 30, 2007

(65) Prior Publication Data

US 2008/0200502 A1 Aug. 21, 2008

Related U.S. Application Data

(63) Continuation of application No. 10/974,028, filed on Oct. 27, 2004, now Pat. No. 7,320,988.

(60) Provisional application No. 60/514,476, filed on Oct. 27, 2003.

(51) Int. Cl.
 *A61K 31/47* (2006.01)
 *A61K 31/195* (2006.01)
(52) U.S. Cl. .................. 514/311; 514/563; 514/564
(58) Field of Classification Search ............... 514/311, 514/563, 564
 See application file for complete search history.

(56) References Cited

U.S. PATENT DOCUMENTS

| 4,603,144 | A | 7/1986 | Campbell |
| 4,661,579 | A | 4/1987 | Blöcker |
| 4,801,610 | A | 1/1989 | Miyano |
| 4,880,794 | A | 11/1989 | Halskov |
| 4,921,997 | A | 5/1990 | Lalezari et al. |
| 5,093,367 | A | 3/1992 | Lalezari et al. |
| 5,268,500 | A | 12/1993 | Lalezari et al. |
| 5,272,176 | A | 12/1993 | Ulrich et al. |
| 5,292,935 | A | 3/1994 | Lalezari et al. |
| 5,602,277 | A | 2/1997 | Babu et al. |
| 5,661,139 | A | 8/1997 | Lankin et al. |
| 5,677,330 | A | 10/1997 | Abraham et al. |
| 5,700,447 | A | 12/1997 | Bucala et al. |
| 5,716,987 | A | 2/1998 | Wille |
| 5,962,651 | A | 10/1999 | Lalezari et al. |
| 6,337,350 | B1 | 1/2002 | Rahbar et al. |
| 6,589,944 | B1 | 7/2003 | Rahbar |
| 6,605,642 | B2 | 8/2003 | Rahbar et al. |
| 7,320,988 | B2 * | 1/2008 | Rahbar et al. ............. 514/311 |
| 2002/0002203 | A1 | 1/2002 | Rahbar et al. |
| 2002/0013256 | A1 | 1/2002 | Rahbar et al. |
| 2002/0123501 | A1 | 9/2002 | Rahbar et al. |
| 2002/0128278 | A1 | 9/2002 | Rahbar et al. |

FOREIGN PATENT DOCUMENTS

| WO | WO 92/07560 A1 | 5/1992 |
| WO | WO 95/31192 A1 | 11/1995 |
| WO | WO 98/55121 A1 | 12/1998 |
| WO | 00/23063 A2 | 4/2000 |
| WO | WO 00/59875 A2 | 10/2000 |
| WO | WO 00/66102 A2 | 11/2000 |
| WO | 01 41709 A2 | 6/2001 |
| WO | WO 01/76584 A2 | 10/2001 |
| WO | WO 02/072083 A1 | 9/2002 |
| WO | WO 02/076443 A1 | 10/2002 |
| WO | 03 070755 A2 | 8/2003 |
| WO | WO 2004/071416 B1 | 11/2004 |

OTHER PUBLICATIONS

Al-Abed et al., "Advanced glycation end products: detection and reversal," *Methods Enzymol.*, 1999; 309:152-172.
Al-Abed, Y. et al., "Inhibition of advanced glycation endproduct formation by acetaldehyde: Role in the cardioprotective effet of ethanol," *Proc. Natl. Acad. Sci. USA*, 1999; 96:2385-2390.
Alderson et al., "The AGE inhibitor pyridoxamine inhibits lipemia and development of renal and vascular disease in Zucker obese rats," *Kidney Int.*, 2003; 63:2123-2133.
Aldrich Catalog 805,786,8, and 3, 1994-1995.
Altomare et al., "Increased lipid peroxidation in type 2 poorly controlled diabetic patients," *Diabetes Metab.*, 1992; 18:264-271.
Anderson et al., "The myeloperoxidase system of human phagocytes generates N-epsilon (carboxymethyl) lysine on proteins: a mechanism for producing advanced glycation end products at sites of inflammation," *J. Clin. Invest.*, 1999; 104:103-113.
Asif, M. et al., "An advanced glycation endproduct cross-link breaker can reverse aga-related increases in myocardial stiffness," *PNAS*, Mar. 14, 2004; 97(6):2809-2813 plus 1 page with correction.
Basta et al., "Advanced glycation end products activate endothelium through signal-transduction receptor RAGE: a mechanism for amplification of inflammatory responses," *Circulation*, 2002; 105:816-822.
Baynes et al., "Glycoxidation and lipoxidation in atherogenesis," *Free Rad. Biol. Med.*, 2000; 28:1708-1716.
Baynes et al., "Perspective in diabetes: role of oxidative stress in diabetic complications. A new perspective on an old paradigm," *Diabetes*, 1999; 48:1-9.
Beisswenger, P.J., et al., "Metformin Reduces Systemic Methylglyoxal Levels in Type 2 diabetes," *Diabetes*, Jan. 1999; 48:198-202.

(Continued)

*Primary Examiner*—Raymond J Henley, III
(74) *Attorney, Agent, or Firm*—Rothwell, Figg, Ernst & Manbeck p.c.

(57) ABSTRACT

This invention relates to methods for lowering lipid levels in mammals using compounds that inhibit advanced glycation endproducts (AGEs), LR-9, LR-74 and LR-90. These compounds, which inhibit non-enzymatic protein glycation, also inhibit the formation of advanced lipoxidation endproducts (ALES) on target proteins by trapping intermediates in glycoxidation and lopoxidation and inhibiting oxidation reactions important in the formation of AGEs and ALEs.

8 Claims, 23 Drawing Sheets

OTHER PUBLICATIONS

Boel, E., et al., "Diabetic Late Complications: Will Aldose Reductase Inhibitors or Inhibitors of Advanced Glycosylation Endproduct Foirmation Hold Promise?," *J. Diabetes and Its Complications*, 1995; 9:104-129.

Booth, A.A. et al., "In Vitro Kinetic Studies of Formation of Antigenic Advanced Glycation End Products (AGEs)," *Journal of Biological Chemistry*, 1997; 272(9):5430-5437.

Booth, A.A. et al., "Thiamine Pyrophosphate and Pyridoxamine Inhibit the Formation of Antigenic Advanced Glycation End-Products: Comparison with Aminoguanidine," *Biochem. Biophys. Res. Commun.*, 1996; 220:113-119.

Boulanger et al., "AGEs bind to mesothelial cells via RAGE and stimulate VCAM-1 expression," *Kidney Int.*, 2002; 61:148-156.

Brownlee, M., "Biochemistry and molecular cell biology of diabetic complications," *Nature*, 2001; 414:813-820.

Bucala et al., "Advanced glycosylation: chemistry, biology and implications for diabetes and aging," *Adv. Pharmacol*, 1992; 23:1-33.

Bucala et al., "Lipid advanced glycation pathway for lipid oxidation in vivo," *Proc. Natl. Acad. Sci. USA*; 1993; 90:6434-6438.

Bucala et al., "Lipid and lipoprotein modification by advanced glycation end-products: Role in atherosclerosis," *Exper. Physiol.*, 1997; 82:327-337.

Bucala et al., "Protein glycation and vascular disease. In: Endocrinology of cardiovascular function," *E.R. Levin and J.L. Nadler (eds.)*. (*1998*) *Kluwer Acad. Publishers*, pp. 159-180.

Bucala et al., "Modification of DNA by reducing sugars: a possible mechanism for nucleic acid aging and age-related dysfunction in gene expression," *Proc. Natl. Acad Sci. USA*, 1984; 81: 105-109.

Calatayud, J.M., "Favorable Effects of the Lipid-Lowering and Platelet Antiaggregant Plafibride on the Ageing Process of Mice of the C57BL/6J Strain," *Math and Find Exptl Clin Pharmacol.*, 1983; 5(10):707-714.

Cameron, J.M., "Favorable Effects of the Lipid-Lowering and Platelet Antiaggregant Plafibride on the Ageing Process of Mice of the C57BL/6J Strain," *Math and Find Exptl Clin Pharmacol.*, 1983; 5(10):707-714.

Carew et al., "Antiatherogenic effect of probucol unrelated to its hypocholesterolemic effect: evidence that antioxidants in vivo can selectively inhibit low density lipoprotein degradation in macrophage-rich fatty streaks and slow the progression of atherosclerosis in the Watanabe heritable hyperlipidemic rabbit," *Proc. Natl. Acad. Sci. USA*, 1987; 84:7725-7729.

Carpenter et al., "Oral α-tocopherol supplementation inhibits lipid oxidation in established human atherosclerotic lesions," *Free Radic. Res.*, 2003; 37:1235-1244.

Chaturvedi et al., "Microalbuminuria in type 1 diabetes: rates, risk factors and glycemic threshold," *Kidney Int.*, 2001; 60:219-227.

Chellan et al., "Protein crosslinking by the Maillard reaction: dicarbonyl-derived imidazolium crosslinks in aging and diabetes," *Arch. Biochem. Biophys.*, 1999; 368:98-104.

Cooper, M.E. et al., "The cross-link breaker, N-phenacylthiazolium bromide prevents vascular advanced glycation end-product accumulation," *Diabetologia*, 2000; 43:660-664.

Corbett, J.A. et al., "Aminoguanidine, a Novel Inhibitor of Nitric Oxide Formation, Prevents Diabetic Vascular Dysfunction," *Diabetes*, 1992; 41:552-556.

Degenhardt et al., "Pyridoxamine inhibits early renal disease and dyslipidemia in the streptozotocin-diabetic rat," *Kidney Int.*, 2002; 61:939-950.

Durany, N. et al., "Investigations on oxidative stress and therapeutical implications in dementia," *Eur. Arch. Psychiatry Clin. Neurosci.*, 1999; 249:Suppl. 3 III/68-III/73.

Ferrari, E. et al., "Effects of long-term treatment (4 years) with pentoxifylline on haemorheological changes and vascular complications in diabetic patients," 1987; 5(1):26-39.

Figarola et al., "LR-90 A New Advanced Glycation Endproduct Inhibitor Prevents Progression of Diabetic Nephropathy In Streptozotocin-Diabetic Rats," *Diabetologia*, vol. 46; pp. 1140-1152 (2003).

Forbes et al., "Reduction of the accumulation of advanced glycation end products by ACE inhibition in experimental diabetic nephropathy," *Diabetes*, 2002; 51:3274-3282.

Friedman, "Advanced glycation end-products in diabetic nephropathy," *Nephrol. Dial. Transplant.*, 1999; 14(Suppl 3):1-9.

Fu et al., "The advanced glycation end product, Nε-(carboxymethyl) lysine, is a product of both lipid peroxidation and glycoxidation reactions," J. Biol. Chem., 1996; 271:9982-9986.

Gogas Yavuz et al., "Effects of aminoguanidine on lipid and protein oxidation in diabeic rat kidneys," *Int. J. Exp. Diabetes Res.*, 2002; 3:145-151.

Grigoleit, H.G. et al., "Red Blood Cell Aging As a Model to Influence Pharmacologically The Red Cell Filterability," *Research in Experimental Medicine*, 1981; 179:249-254.

Guarnieri, G. et al., "Modulation of Protein Kinetics in Chronic Renal Failure," *Miner Electrolyte Metab*, 1997; 23:214-217.

Hedrick et al., "Glycation impairs high-density lipoprotein function," *Diabetologia*, 2000; 43:312-320.

Heinecke, "Oxidants and antioxidants in the pathogenesis of atherosclerosis: implications for the oxidized low density lipoprotein hypothesis," *Atherosclerosis*, 1998; 141:1-15.

Hicks et al., "Catalysis of lipid peroxidation by glucose and glycosylated collagen," *Biochem. Biophys. Res. Commun.*, 1988; 151:649-655.

Hirsch, J. et al., "The reaction of some dicarbonyl sugars with aminoguanidine," *Carbohydrate Research*, 1992; 232:125-130.

Horie et al., "Immunohistochemical colocalization of glyoxidation products and lipid peroxidation products in diabetic renal glomerular lesions," *J. Clin. Invest.*,1997; 100:2995-3004.

Ihm et al., "Effect of aminoguanidine on lipid peroxidation in streptozotocin-induced diabetic rats," *Metabolism*, 1999; 48:1141-1145.

Inouye et al., "Glycated hemoglobin and lipid peroxidation in erythrocytes of diabetic patients," *Metabolism*, 1999; 48:205-209.

Iwafune, Y. et al., "Clinical use of pentoxifylline in haemorrhagic disorders of the retina," *Pharmatherapeutica*, 1980; 2:429-438.

Jain et al., "Erythrocyte membrane lipid peroxidation and glycosylated hemoglobin in diabetes," *Diabetes*,1989; 38:1539-1543.

Jakus, V. et al., "Inhibition of Nonenzymatic Protein Glycation and Lipid Peroxidation by Drugs with Antioxidant Activity," *Life Sciences*, 1999; 65(18-19):1991-1993.

Januszewski et al., "Role of lipids in chemical modification of proteins and development of complications in diabetes," *Biochem. Soc. Trans.*, 2003; 31:1413-1416.

Jenkins et al., "Lipoproteins in the DCCT/EDIC cohort: associations with diabetic nephropathy," *Kidney Int*, 2003; 64:817-828.

Jyothirmayi, G.N. et al., "Effects of Metformin on Collagen Glycation and Diastolic Dysfunction in Diabetic Myocardium," *J. Cardiovasc. Pharmacol. Therapeut.*, 1998; 3(4):319-326.

Kennedy et al., "Glycation, oxidation, and lipoxidation in the development of diabetic complications," *Metabolism*, 1997; 46:14-21.

Khalifah, R.G., "Amadorins: Novel Post-Amardori Inhibitors of Advanced Glycation Reactions," *Biochem. Biophys. Res. Commun.*, 1999; 257;251-258.

Kislinger et al., "N(epsilon)-(carboxymethyl)lysine adducts of proteins are ligands for receptor for advanced glycation end products that activate cell signaling pathways and modulate gene expression," *J. Biol. Chem.*, 1999; 274:31740-31749.

Knott et al., "Glycation and glycoxidation of low-density lipoproteins by glucose and low-molecular mass aldehydes. Formation of modified and oxidized particles," *Eur. J. Biochem.*, 2003; 270:3572-3582.

Kochakian, M. et al., "Chronic Dosing with Aminoguanidine and Novel Advanced Glycosylation End Product-Formation Inhibitors Ameliorates Cross-Linking of Tail Tendon Collagen and STZ-Induced Diabetic Rats," *Diabetes*, 1996; 45:1694-1700.

Kushiro et al., "Accumulation of N sigma-(carboxy-methyl)lysine and changes in glomerular extracellular matrix components in Otsuka Long-Evans Tokushima fatty rat: a model of spontaneous NIDDM," *Nephron*, 1998; 79:458-468.

Lalezari, I. et al., "LR16, a compound with potent effects on the oxygen affinity of hemoblogin, on blood cholesterol, and on low density lipoprotein," *Proc. Natl. Acad. Sci. USA*, Aug. 1988; 85:6117-6121.

Lalezari, I. et al., "Synthesis and Investigation of Effects of 2-[4-[[(Arylamino)carbonyl]amino]phenoxy]-2-methylpropionic Acids on the Affinity of Hemoglobin of Oxygen: Structure-Activity Relationship," *J. Med. Chem.*, 1989p; 32:2352-2357.

Lam et al., "Cholesterol-lowering therapy may retard the progression of diabetic nephropathy," *Diabetologia*, 1995; 38:604-609.

Lee, Y. et al., "The Effect of Pentoxifylline on Current Perception Thresholds in Patients With Diabetic Sensory Neuropathy," *Journal of Diabetes and Its Complications*, 1997; 11:274-278.

Lyons et al., "Glycation, oxidation and lipoxidation in the development of the complications of diabetes mellitus: a 'carbonyl stress' hypothesis," *Diabetes Rev.*, 1997; 5:365-391.

Makita et al., "Advanced glycosylation end products in patients with diabetic nephropathy," *N. Eng. J. Med.*, 1991; 325:836-842.

Malik, N.S. and Meek, K.M., "The Inhibition of Sugar-Induced Structural Alterations in Collagen by Aspirin and Other Compounds," *Biochem. Biophys. Res. Commun.*, 1994; 199(2):683-686.

Marques, C. et al., "Bendazac decreases in vitro glycation of human lens crystallins. Decrease of in vitro protein glyction by bendazac," *Documenta Ophthalmologica*, 1995; 90:395-404.

Matsumoto et al., "Immunohistochemical evidence for increased formation of advanced glycation end products and inhibition by aminoguanidine in diabetic rat lines," *Biochem. Biophys. Res. Commun.*, 1997; 241:352-354.

McCarty, M.F., "Nitric oxide deficiency, leukocyte activation, and resultant ischemia are crucial to the pathogenesis of diabetic retinopathy/neuropathy-preventive potential of antioxidants, essential fatty acids, chromium, ginkgolides, and pentoxifylline," *Medical Hypotheses*, 1998; 50:435-449.

Medline Abstract No. 97217050, Kumar, Indian Journal of Experimental Biology, (May 1996) 34(5), 391-402.

Medline Abstract No. 96432582, Oka et al., Japanese Journal of Pharmacology, (Jun 1996) 71(2), 89-100.

Medline Abstract No. 97074593, Smith et al., CA: A Cancer Journal for Clinicians, (Nov.-Dec. 1996), 46(6), 343-63.

Menzel, E.J. et al., "Comparison of the effect of different inhibitors on the non-enzymatic glycation of rat tail tendons and bovine serum albumin," *Ann. Clin. Biochem.*, 1996; 33:241-248.

Metz et al., "Pyridoxamine traps intermediates in lipid peroxidation reactions in vivo: evidence on the role of lipids in chemical modification of protein and development of diabetic complications," *J. Biol. Chem.*, 2003; 278:42012-42019.

Metz et al., "Pyridoxamine, an inhibitor of advanced glycation and lipoxidation reactions: a novel therapy for treatment of diabetic complications," *Arch. Biochem. Biophys.*, 2003; 419: 41-49.

Miwa, I. et al., "Inhibition of Advanced Protein Glycation by 8-Quinolinecarboxylic Hydrazide," *Pharmacology*, 1996; 52:314-320.

Miyata et al., "Advanced glycation and lipoxidation end products: role of reactive carbonyl compounds generated during carbohydrate and lipid metabolism," *J. Am. Soc. Nephrol.*, 2000; 11:1744-1752.

Miyata et al., "Angiotensin II receptor antagonists and angiotensin-converting enzyme inhibitors lower in vitro the formation of advanced glycation end products: biochemical mechanisms," *J. Am. So. Nephrol.*, 2002; 13:2478-2487.

Miyata et al., "Angiotensin II receptor blockers and angiotensin converting enzyme inhibitors: implication of radical scavenging and transition metal chelation in inhibition of advanced glycation end product formation," *Arch. Biochem. Biophys.*, 2003; 419:50-54.

Miyata et al., "Generation of protein carbonyls by glycoxidation and lipoxidation reactions with autoxidation products of ascorbic acid and polyunsaturated fatty acids," *FEBS Lett.*, 1998; 437:24-28.

Morimitsu, Y. et al., "Protein Glycation Inhibitors from Thyme (*Thymus vulgaris*)," *Biosci. Biotech. Biochem.*, 1995; 59(11):2018-2021.

Mullarkey et al., "Free radical generation by early glycation products: a mechanism for accelerated atherogenesis in diabetes," *Biochem. Biophys. Res. Commun.*, 1990; 173:932-939.

Münch, G. et al., "Advanced glycation endproducts in aging and Alzheimer's disease," *Brain Research Reviews*, 1997; 23:134-143.

Münch, G. et al., "Influence of advanced glycation end-products and AGE-inhibitors on nucleation-dependent polymerization of β-amyloid peptide," *Biochimica et Biophysica Acta*, 1997; 1360:17-29.

Muntner et al., "Plasma lipids and risk of developing renal dysfunction: the atherosclerosis risk in communities study," *Kidney Int*, 2000; 58:293-301.

Nangaku et al., "Anti-hypertensive agents inhibit in vivo the formation of advanced glycation end products and improve renal damage in a type 2 diabetic nephropathy rat model," *J. Am. Soc. Nephrol.*, 2003; 14:1212-1222.

Nakamura, S. et al., "Progression of Nephropathy in Spontaneous Diabetic Rats is Prevented by OPB-9195, a Novel Inhibitor of Advanced Glycation," *Diabetes*, 1997; 46:895-899.

Navarro, J.F. et al., "Pentoxifylline (PTF) reduces proteinuria and tumor necrosis factor-alpha (TNFa) in diabetic patients with advanced renal failure," *J. of the American Society of Nephrology*, 1998; 9:120A.

Ortwerth et al., "The generation of superoxide anions in glycation reactions with sugars, osones, and 3-deoxyosones," *Biochem. Biophys. Res. Commun.*, 1998; 245:161-165.

Parnetti, L. et al., "The role of haemorheological factors in the aging brain: long-term therapy with pentoxifylline ('Trental' 400) in elderly patients with initial mental deterioration," *Pharmatherapeutica*, 1986; 4:617-627.

Poirier et al., "Oxidative stress occurs in absence of hyperglycaemia and inflammation in the onset of kidney lesions in normotensive obese rats," *Nephrol. Dial. Transplant.*, 2000; 15:467-476.

Price, D.L. et al., "Chelating Activity of Advanced Glycation Endproduct Inhibitors," *The Journal of Bilogical Chemistry*, vol. 276, No. 52, pp. 48967-48972 (Dec. 28, 2001).

Price et al., "Chelating activity of Advanced Glycation Endproducts Inhibitors," *The Journal of Bilogical Chemistry*, 2001; 276:48967-48972.

Qiang, X. et al., "Inhibitory effect of troglitazone on diabetic neuropathy in streptozotocin-induced diabetic rats," *Diabetologia*, 1998; 41:1321-1326.

Rahbar, S. et al., "A new rapid method to detect inhibition of Amadori product generated by δ-gluconolactone," *Clinica Chimica Acta*, 1999; 123-130.

Rahbar, S. et al., "Evidence that pioglitazone, metformin and pentoxifylline are inhibitors of glycation," *Clin. Chim Acta.*, 2000; 301(1-2):65-77.

Rahbar et al., "Inhibitors and breakers of advanced glycation endproducts (AGEs): a review," *Curr. Med. Chem. B Immunol. Endocr. Metabol. Agents*, 2002; 2:135-161.

Rahbar, S. et al., "Novel Inhibitors of Advanced Glycation Endproducts," *Biochemical and Biophysical Research Communications*, 1999; 262:651-656.

Rahbar et al., "Novel Inhibitors of Advanced Glycation Endproducts (Part II), *Molecular Cell Biology Research Communications*," vol. 3, pp. 360-366 (2000).

Rahbar et al., "Novel inhibitors of Advanced Glycation Endproducts," *Biochemical and Biophysical Research Communications*, 2003; 419:63-79.

Raj, D.S.C. et al., "Advanced Glycation End Products: A Nephrologist's Perspective," *American Journal of Kidney Diseases*, Mar. 2000, 35(3):365-380.

Requena et al., "Carboxymethylethanolamine: a biomarker of phospholipid modification during the Maillard reaction in vivo," *J. Biol. Chem.*, 1997; 272:17473-14779.

Requena et al., "Lipoxidation products as biomarkers of oxidative damage to proteins during lipid peroxidation reactions," *Nephrol. Dial. Transplant.*, 1996; 11(Suppl 5):48-53.

Ruggiero-Lopez, D. et al., "Reaction of Metformin with Dicarbonyl Compounds. Possible Implication in the Inhibition of Advanced Glycation End Product Formation," *Biochemical Pharmacology*, 1999; 58:1765-1773.

Ryan, M.E. et al., "Tetracyclines Inhibit Protein Glycation in Experimental Diabetes," *Adv. Dent. Res.*, 1998; 12:152-158.

Sakurai et al., "Superoxide production from nonenzymatically glycated protein," *FEBS Lett.*, 1988; 236:406-410.

Sensi, M. et al., "D-Lysine reduces the non-enzymatic glycation of proteins in experimental diabetes mellitus in rats," *Diabetologia*, 1993; 36:797-801.

Sheetz et al., "Molecular understanding of hyperglycemia=s adverse effects for diabetic complications," *JAMA*, 2002; 288: 2579-2588.

Singh et al., "Advanced glycation end-products: a review," *Diabetologia*, 2001; 44:129-146.

Soulis, T. et al. "A novel inhibitor of advanced glycation end-product formation inhibits mesenteric vascular hypertrophy in experimental diabetes," *Diabetologia*, 1999; 42:472-479.

Soulis, T. et al. "Relative contributions of advanced glycation and nitric oxide synthase inhibition to aminoguanidine-mediated renoprotection in diabetic rats," *Diabetologia*, 1997; 40:1141-1151.

Stefek et al., p-Dimethyl aminobenzaldehyde-reactive substances in tail tendon collagen of streptozotocin-diabetic rats: temporal relation to biomechanical properties and advanced glycation endproduct (AGE)-related fluorescenc, *Biochim. Biophys. Acta*, 2000; 1502:398-404.

Stitt et al., "Advanced glycation end products and diabetic complications," *Expert Opin. Invest. Drugs*, 2002; 11:1205-1223.

Swamy-Mruthinti, S. et al., "Acetyl-L-Carnitine Decreases Glycation of Lens Proteins: In vitro Studies," *Exp. Eye Res.*, 1999; 69:109-115.

Taguchi, T. et al., "Inhibition of advanced protein glycation by a Schiff base between aminoguanidine and pyridoxal," *European Journal of Pharmacology*, 1999; 378:283-289.

Tanaka, Y. et al., "Effect of metformin on advanced glycation endproduct formation and peripheral nerve function in streptozotocin-induced diabetic rats," *European Journal of Pharmacology*, 1999; 376:17-22.

The Diabetes Control and Complications Trial Research Group (1993). The effect of intensive treatment of diabetes on the development and progression of long-term complications in insulin-dependent diabetes mellitus, *N. Engl. J. Med.*, 1993; 329:977-986.

The Merck Index, paragraphs 462, 1927 and 4857, 1996.

Thornalley et al., "Formation of glyoxal, methylglyoxal and 3-deoxyglucosone in the glycation of proteins by glucose," *Biochem. J.*, 1999; 344:109-116.

Thornalley et al., "Kinetics and mechanism of the reaction of aminoguanidine with the alpha-oxoaldehydes glyoxal, methylglyoxal, and 3-deoxyglucosone under physiological conditions," *Biochem. Pharmacol.*, 2000; 60:55-65.

Thornalley, P.J. et al., "Rapid Hydrolysis and Slow $\alpha,\beta$-Dicarbonyl Cleavage of an Agent Proposed to Cleave Glucose-Derived Protein Cross-Links," *Biochemical Pharmacology*, 1999; 57:303-307.

Thorpe et al., "Maillard reaction products in tissue proteins: new products and new perspectives," *Amino Acids*, 2003; 25:275-281.

Tilton, R.G. et al., "Prevention of Diabetic Vascular Dysfunction by Guanidines. Inhibition of Nitric Oxide Synthase Versus Advanced Glycation End-Product Formation," *Diabetes*, 1993; 42:221-232.

Tsuchida, K. et al., "Suppression of transforming growth factor beta and vascular endothelial growth factor in diabetic nephropathy in rats by a novel advanced glycation end product inhibitor, OPB-9195," *Diabetologia*, 1999; 42:579-588.

Uchida et al., "Protein modification by lipid peroxidation products: formation of malondialdehyde-derived N(epsilon)-(2-propenol) lysine in proteins," *Arch. Biochem. Biophys.*, 1997; 346:45-52.

Ulrich, P. et al., "Pharmacological reversal of advanced glycation end-product-mediated protein crosslinking," *Diabetologia*, 1997; 40:S157-S159.

Ulrich et al., "Protein glycation, diabetes & aging," *Recent Prog. Horm. Res.*, 2001; 56:1-21.

United Kingdom Prospective Diabetes Study (UKPDS: 10) (1993) Urinary albumin excretion over 3 years in diet-treated Type 2, (non-insulin dependent) diabetic patients, and association with hypertension, hyperglycemia and hypertriglyceridaemia. *Diabetologia*, 1993; 36:1021-1029.

United Kingdom Prospective Diabetes Study Group (1998). Intensive blood-glucose control with sulphonylureas or insulin compared with conventional treatment and risk of complications in patients with type 2 diabetes (UKPDS 33). *Lancet*, 1998; 352:837-853.

van Boekel, A.M. et al., "Glycation of human serum albumin: inhibition by Diclofenac," *Biochimica et Biophysica Acta*, 1992; 1120:201-204.

van Leiden et al., Blood pressure, lipids, and obesity are associated with retinopathy: the Hoorn Study, *Diabetes Care*, 2002; 25: 1320-1325.

Vasan, S. et al., "An agent cleaving glucose-derived protein crosslinks in vitro and in vivo," *Nature*, 1996; 382:275-278.

Vlassara et al., "Advanced glycation end-products induce glomerular sclerosis and albuminuria in normal rats," *Proc. Natl. Acad. Sci. USA*, 1994; 91:11704-11708.

Vlassara et al., "Diabetes and advanced glycation endproducts," *J. Intern. Med.*, 2002; 251:87-101.

Vlassara, "The AGE-receptor in the pathogenesis of diabetic complications," *Diabetes Metab. Res. Rev.*, 2001; 17:436-443.

Voziyan, P. A. et al., "A Post-Amadori Inhibitor Pyridoxamine Also Inhibits Chemical Modification of Proteins by Scavenging Carbonyl Intermediates of Carbohydrate and Lipid Degradation," *The Journal of Biological Chemistry*, 2002; 5:3397-3403.

Voziyan et al., "Modification of proteins In vitro by physiological levels of glucose: Pyridoxamine inhibits conversion of amadori intermediate to advanced glycation end-products through binding of redox metal ions," *J. Biol. Chem.*, 2003; 278:46616-46624.

Wautier et al., "Activation of NADPH oxidase by AGE links oxidant stress to altered gene expression via RAGE," *Am. J. Physiol. Endocrinol. Metab.*, 2001; 280:E685-E694.

Wendt et al., "RAGE drives the development of glomerulosclerosis and implicates podocyte activation in the pathogenesis of diabetic nephropathy," *Am. J. Pathol.*, 2003; 162:1123-1137.

Wilkinson-Berka et al., "ALT-946 and aminoguanidine, inhibitors of advanced glycation, improve severe nephropathy in the diabetic transgenic (mREN-2) 27 rat," *Diabetes*, 2002; 51:3283-3289.

Wolffenbuttel, B.H.R. et al., "Breakers of advanced glycation end products restore large artery properties in experimental diabetes," *Proc. Natl. Acad. Sci. USA*, 1998; 95:4630-4634.

Yan et al., "Glycation, inflammation, and RAGE: a scaffold for the macrovascular complications of diabetes and beyond," *Circ. Res.*, 2003; 93:1159-1169.

Yim et al., "Free radicals generated during the glycation reaction of amino acids by methylglyoxal. A model study of protein-cross-linked free radicals," *J. Biol. Chem.*, 1995; 270:28228-28233.

Zheng et al., "Prevention of diabetic nephropathy in mice by a diet low in glycoxidation products," *Diabetes Metab. Res. Rev.*, 2002; 18:224-237.

European Search Report dated Dec. 10, 2007, 04796420.0, Applicant—City of Hope, search completed Nov. 29, 2007, 5 pages.

\* cited by examiner

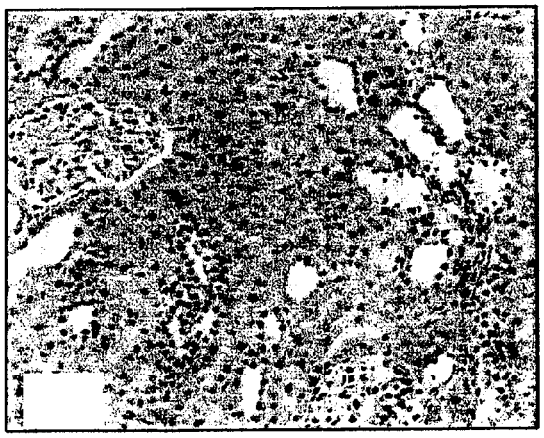 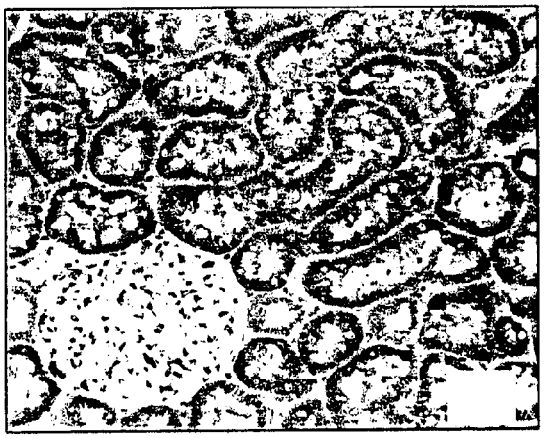
FIG. 22A  FIG. 22B
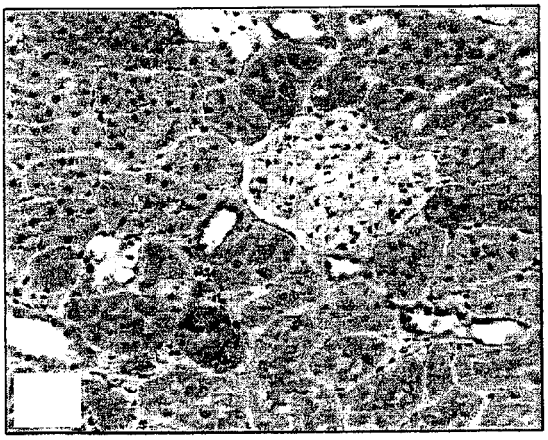 
FIG. 22C  FIG. 22D

METHODS OF LOWERING LIPID LEVELS IN A MAMMAL

This application is a continuation of U.S. application Ser. No. 10/974,028, filed Oct. 27, 2004, now U.S. Pat. No. 7,320,988, which claims benefit of U.S. Provisional Application No. 60/514,476, filed Oct. 27, 2003. The disclosures of each of the above applications are hereby incorporated by reference in their entireties into the present application.

BACKGROUND OF THE INVENTION

1. Technical Field

This application relates to the field of biomedical sciences, and in particular relates to methods for lowering lipid levels in mammals. Some embodiments are directed to inhibition comprising administering compounds such as 4-(2-napthylcarboxamido) phenoxyisobutyric acid]; 2-(8-quinolinoxy) propionic acid]; and methylene bis(4,4'-(2-chlorophenylureidophenoxyisobutyric acid)].

2. Description of the Background Art

The Diabetic Control and Complications Trial (DCCT) and UKPDS studies have identified hyperglycemia as the main risk factor for the development of diabetic complications. The Diabetes Control and Complications Trial Research Group *N. Engl. J. Med.* 329:977-986, 1993; UK Prospective Diabetes Study *Group Lancet* 352:837-853, 1998. Formation of advanced glycation endproducts (AGEs) has been identified as the major pathogenic link between hyperglycemia and the long-term complications of diabetes. Makita et al., *N. Eng. J. Med.* 325:836-842, 1993; Bucala and Cerami, *Adv. Pharmacol* 23:1-33, 1992; Browlee, *Nature* 414:813-820, 2001; Sheetz and King, *J.A.M.A.* 288:2579-2588, 2002; Stith et al., *Expert Opin. Invest. Drugs* 11:1205-1223, 2002.

Non-enzymatic glycation (also known as the Maillard reaction) is a complex series of reactions between reducing sugars and the amino groups of proteins, lipids, and DNA which leads to browning, fluorescence, and cross-linking. Bucala et al., *Proc. Natl. Acad. Sci. USA* 90:6434-6438, 1993; Bucala et al., *Proc. Natl. Acad. Sci. USA* 81:105-109, 1984; Singh et al., *Diabetologia* 44:129-146, 2001. This complex cascade of condensations, rearrangements and oxidation produces heterogeneous, irreversible, proteolysis-resistant, antigenic products known as advanced glycation endproducts (AGEs). Singh et al., *Diabetologica* 44:129-146, 2001; Ulrich and Cerami, *Rec. Prog. Hormone Res.* 56:1-2, 2001. Examples of these AGEs are $N^\epsilon$-(carboxymethyl)lysine (CML), $N^\epsilon$-(carboxyethyl)lysine (CEL), $N^\epsilon$-(carboxymethyl)cysteine (CMC), arg-pyrimidine, pentosidine and the imidazolium crosslinks methyl-gloxal-lysine dimer (MOLD) and glyoxal-lysine dimer (GOLD). Thorpe and Baynes, *Amino Acids* 25:275-281, 2002; Chellan and Nagaraj, *Arch. Biochem. Biophys.* 368:98-104, 1999. This type of glycation begins with the reversible formation of a Schiff's base, which undergoes a rearrangement to form a stable Amadori product.

Both Schiff's bases and Amadori products further undergo a series of reactions through dicarbonyl intermediates to form AGEs. Lipid peroxidation of polyunsaturated fatty acids (PUFA), such as arachidonic acid and linoleic acid, also yield carbonyl compounds. Some of these are identical to those formed from carbohydrates, such as MG and GO, and others are characteristic of lipid, such as malondialdehyde (MDA), 4-hydroxynonenal (HNE), and 2-hydroxyheptanal (2HH). See Baynes and Thorpe, *Free Rad. Biol. Med.* 28:1708-1716, 2000; Fu et al., *J. Biol. Chem.* 271:9982-9986, 1996; Miyata et al., *FEBS Lett.* 437:24-28, 1998; Miyata et al., *J. Am. Soc. Nephrol.* 11:1744-1752, 2000; Requena et al., *Nephrol. Dial. Transplant.* 11 (supp. 5):48-53, 1996; Esterbauer et al., *Free Radic. Biol. Med.* 11:81-128, 1991; Requena et al., *J. Biol. Chem.* 272:17473-14779, 1997; Slatter et al., *Diabetologia* 43:550-557, 2000. These reactive carbonyl species (RCSs) rapidly react with lysine and arginine residues of proteins, resulting in the formation of advanced lipoxidation endproducts (ALEs) such as $N^\epsilon$-carboxymethyllysine (CML), N-carboxyethyllysine (CEL), GOLD, MOLD, malondialdehydelysine (MDA-lysine), 4-hydroxynonenal-lysine (4-HNE-lysine), hexanoyl-lysine (Hex-lysine), and 2-hydroxyheptanoyl-lysine (2HH-lysine). See FIG. 1. Thorpe and Baynes, Amino Acids 25:275-281, 2002; Miyata et al., *FEBS Lett.* 437:24-28, 1998; Miyata et al., *J. Am. Soc. Nephrol.* 11:1744-1752, 2000; Uchida et al., *Arch. Biochem. Biophys.* 346:45-52, 1997; Baynes and Thorpe, *Free Rad. Biol. Med.* 28:1708-1716, 2000. Since CML, CEL, GOLD and MOLD can result from lipid and carbohydrate metabolism, these chemical modifications on tissue proteins that can serve as biomarkers of oxidative stress resulting from sugar and lipid oxidation. Fu et al., *J. Biol. Chem.* 271:9982-9986, 1996; Requena et al., *Nephrol. Dial. Transplant.* 11 (supp. 5):48-53, 1996. The relative role of hyperglycemia versus hyperlipidemia in the chemical modification and pathogenesis of diabetic complications remains uncertain, however. Additionally, several biomarkers of protein modification such as CML and CEL can be derived from either sugar or lipid sources, further complicating the interpretation and analysis of experimental data.

In human diabetic patients and in animal models of diabetes, these non-enzymatic reactions are accelerated and cause accumulation of AGEs on long-lived structural proteins such as collagen, fibronectin, tubulin, lens crytallin, myelin, laminin and actin, in addition to hemoglobin, albumin, LDL-associated proteins and apoprotein. The structural and functional integrity of the affected molecules, which often have major roles in cellular functions, are perturbed by these modifications, with severe consequences on organs such as kidney, eye, nerve, and micro-vascular functions, which consequently leads to various diabetic complications such as nephropathy, atherosclerosis, microangiopathy, neuropathy and retinopathy. Boel et al., *J. Diabetes Complications* 9:104-129, 1995; Hendrick et al., *Diabetologia* 43:312-320, 2000; Vlassara and Palace, *J. Intern. Med.* 251:87-101, 2002.

Current research indicates that reactive carbonyl species such as MGO, GO, GLA, dehydroascorbate, 3-deoxyglucosone and malondialdehyde, are potent precursors of AGE/ALE formation and protein crosslinking. Lyons and Jenkins, *Diabetes Rev.* 5:365-391, 1997; Baynes and Thorpe, *Diabetes* 48:1-9, 1999; Miyata et al., *J. Am. Soc. Nephrol.* 11:1744-1752, 2000; Thornalley st al., *Biochem. J.* 344:109-116, 1999. In vitro studies further suggest that these carbonyls originate mainly formed from ascorbate and polyunsaturated fatty acids and not from glucose per se. Miyata et al., *FEBS Lett.* 437:24-28, 1993.

Direct evidence implicates the contribution of AGEs/ALEs in the progression of diabetic complications in different lesions of the kidneys, the rat lens, and in atherosclerosis. Horie et al., *J. Clin. Invest.* 100:2995-3004, 1997; Matsumoto et al., *Biochem. Biophys. Res. Commun.* 241:352-354, 1997; Bucala and Vlassara, *Exper. Physiol.* 82:327-337, 1997; Bucala and Rahbar, in: *Endocrinology of Cardiovascular Function*. E. R. Levin and J. L. Nadler (eds.), 1998. Kluwer Acad. Publishers, pp. 159-180; Horie et al., *J. Clin. Invest.* 100:2995-3004, 1997; Friedman, *Nephrol. Dial. Transplant.* 14 (supp. 3):1-9, 1999; Kushiro et al., *Nephron* 79:458-468, 1998. Several lines of evidence indicate that hyperglycemia in diabetes causes the increase in reactive carbonyl species (RCS) such as methylglyoxal, glycolaldehyde, glyoxal, 3-deoxyglucosone, malondialdehyde, and hydroxynonenal. "Carbonyl stress" leads to increased modification of proteins and lipids, through reactive carbonyl intermediates forming adducts with lysine residues of proteins, followed by oxidative stress and tissue damage. Lyons and Jenkins, *Diabetes Rev.* 5:365-391, 1997; Baynes and Thorpe, *Diabetes* 48:1-9, 1999; Miyata et al., *J. Am. Soc. Nephrol.* 11:1744-1752, 2000. See FIG. 1.

A number of recent clinical trials such as the DCCT/EDIC, EURODIAB Prospective Complications Study Group, the Hoorn Study and UKPDS, have unanimously identified plasma trigylceride concentrations as an independent risk for development of diabetic complications (retinopathy, nephropathy, cardiovascular disease) in diabetic individuals and in the non-diabetic population. Jenkins et al., *Kidney Int.* 64:817-828, 2003; Chaturvedi et al., *Kidney Int.* 60:219-227, 2001; van Leiden et al., *Diabetes Care* 25:1320-1325, 2002; United Kingdom Prospective Diabetes Study (UKPDS: 10), *Diabetologia.* 36:1021-1029, 1993. These studies have established a strong correlation between microalbuminuria and levels of plasma triglycerides and cholesterol. Moreover, recent studies on the lipid-lowering effects of pyridoxamine (PM) and aminoguanidine (AG), two known AGE inhibitors in diabetic and hyperlipidemic rats (Degenhardt et al., *Kidney Int.* 61:939-950; 2002; Alderson et al., *Kidney Int.* 63:2123-2133, 2003), suggested that there was increased lipid peroxidation in these animals and that PM and AG in fact had lipid-lowering effects. Furthermore, the lipid lowering effects of PM and the correlation of plasma triglycerides and cholesterol with AGEs in skin collagen suggested that lipids might be an important source of AGEs in diabetic rats. Several PM adducts of lipoxidation intermediates of arachidonic acid and linoleic acid were excreted in substantially higher concentrations in the urine of diabetic and hyperlipemic rats treated with PM, suggesting an increase in lipoxidation in these animals. Metz et al., *J. Biol. Chem. [August* 15, Epub ahead of print], 2003. Based on these results, the authors concluded that lipids could be the primary source of chemical modification of proteins in diabetes and obesity, especially in the presence of hyperlipidemia or dyslipidemia, even in the absence of hyperglycemia. Alderson et al., *Kidney Int.* 63:2123-2133, 2003; Metz et al., *J. Biol. Chem. [August* 15, Epub ahead of print], 2003.

Over the years, several natural and synthetic compounds have been proposed and advanced as potential AGE/ALE inhibitors. These include aminoguanidine, pyridoxamine, OPB-9195, carnosine, metformin, as well as some angiotensin-converting enzyme inhibitors (ACEI) and angiotensin II type 1 receptor blockers (ARB), derivatives of aryl (and heterocyclic) ureido, and aryl (and heterocyclic) carboxamido phenoxyisobutyric acids. Rahbar et al., *Biochem. Biophys. Res. Commun.* 262:651-656, 1999; Rahbar et al., *Mol. Cell. Biol. Res. Commun.* 3:360-366, 2000; Rahbar and Figarola, *Curr. Med. Chem.* (Immunol. Endocr. Metabol. Agents) 2:135-161, 2002; Rahbar and Figarola, *Curr. Med. Chem.* (Immunol. Endocrin. Metabol.) 2:174-186, 2002; Forbes et al., *Diabetes* 51:3274-3282, 2002; Metz et al., *Arch. Biochem. Biophys.* 419:41-49; Nangaku et al., *J. Am. Soc. Nephrol.* 14:1212-1222, 2003; Rahbar and Figarola, *Arch. Biochem. Biophys.* 419:63-79, 2003. Recently, some of these compounds were found to be effective AGE inhibitors in vivo and to prevent the development of diabetic nephropathy in a streptozotocin-induced diabetes.

Over the last decade, evidence has accumulated implicating AGEs/ALEs as major factors in the pathogenesis of diabetic nephropathy and other complications of diabetes. Administration of AGEs to non-diabetic rats leads to glomerulosclerosis and albuminuria, indicating that AGEs alone may be sufficient to cause renal injury in diabetes. Vlassara et al., *Proc. Natl. Acad. Sci. USA* 91:11704-11708, 1994. Diabetic animals fed with a diet low in glycoxidation products developed minimal symptoms of diabetic nephropathy compared with animals fed with diet high in glycoxidation products. Zheng et al., *Diabetes Metab. Res. Rev.* 18:224-237, 2002. It is widely accepted that AGEs/ALEs contribute to diabetic tissue injury by at least two major mechanisms. Browlee, *Nature* 414:813-820, 2001; Stith et al., Expert Opin. Invest. Drugs 11:1205-1223, 2002; Vlassara and Palace, *J. Intern. Med.* 251:87-101, 2002. The first is receptor-independent alterations of the extracellular matrix architecture and function of intracellular proteins by AGE/ALE formation and AGE/ALE-protein crosslinking. The other is receptor-dependent modulation of cellular functions through interaction of AGE with various cell surface receptors, especially RAGE. Wendt et al., *Am. J. Pathol.* 162:1123-1137, 2003; Vlassara, *Diabetes Metab. Res. Rev.* 17:436-443, 2001; Kislinger et al., *J. Biol. Chem.* 274:31740-3174, 1999.

Advanced glycation/lipoxidation endproducts (AGEs/ALEs) also have been implicated in the pathogenesis of a variety of debilitating diseases such as atherosclerosis, Alzheimer's and rheumatoid arthritis, as well as the normal aging process. The pathogenic process is accelerated when elevated concentrations of reducing sugars or lipid peroxidation products are present in the blood and in the intracellular environment such as occurs with diabetes. Both the structural and functional integrity of the affected molecules become perturbed by these modifications and can result in severe consequences in the short and long term. Because hyperlipidemia, hyperglycemia, diabetes and syndromes such as "metabolic syndrome" are common and are a common cause of morbidity and mortality, methods to counteract the symptoms and consequences of these metabolic states are needed in the art.

SUMMARY OF THE INVENTION

Accordingly, in one embodiment the invention provides a method of lowering lipid levels in a mammal comprising administering to the mammal an effective amount of any of the following compounds or pharmaceutically acceptable salts thereof: LR-9 [4-(2-napthylcarboxamido) phenoxyisobutyric acid]; LR-74 [2-(8-quinolinoxy) propionic acid]; and LR-90 [methylene bis(4,4'-(2-chlorophenylureidophenoxyisobutyric acid)].

In another embodiment, the invention provides a method of treating complications resulting from diabetes which result from elevated levels of lipids, the method comprising administering an effective amount of any of the following compounds or pharmaceutically acceptable salts thereof: LR-9 [4-(2-napthylcarboxamido) phenoxyisobutyric acid]; LR-74 [2-(8-quinolinoxy) propionic acid]; and LR-90 [methylene bis (4,4'-(2-chlorophenylureidophenoxyisobutyric acid)].

In yet another embodiment, the invention provides a method of treating a patient with Menkes Disease, Wilson's Disease, or X-linked Cutis Laxa, which comprises administering an effective amount of any of the following compounds or pharmaceutically acceptable salts thereof: LR-9 [4-(2-napthylcarboxamido) phenoxyisobutyric acid]; LR-74 [2-(8-quinolinoxy) propionic acid]; and LR-90 [methylene bis(4, 4'-(2-chlorophenylureidophenoxyisobutyric acid)].

In in vivo studies investigating the effects of three compounds (LR-9, LR-74 and LR-90) in streptozotocin-induced diabetic rats, the compounds of the present invention not only were able to inhibit the process of AGE formation and prevent early renal disease, but also inhibited the formation of advanced lipoxidation endproducts (ALEs) during lipoxidation reactions and efficiently reduced the increased concentrations of triglycerides and cholesterol in diabetic animals by more than 50%, preventing the complications normally seen in diabetes and in aging.

BRIEF DESCRIPTION OF THE DRAWINGS

FIG. 7 shows the effect of LR compounds on rat tail tendon crosslinking measured by pepsin digestion (fluorescence).

FIG. 11 is series of photographs of trichrome-stained kidney sections showing collagen deposition and cortical tubule degeneration in kidneys from non-diabetic, diabetic and diabetic rats treated with LR-90. Formalin-fixed kidney sections rats from each treatment group at 32 weeks were mounted on slides and stained with trichrome.

FIG. 12 is a series of photographs of picrosirius red-stained kidney sections showing collagen deposition in kidney. Formalin-fixed kidney sections rats from each treatment group at 32 weeks were mounted on slides and stained with Picrosirius red.

FIG. 13 shows immunohistochemical staining for AGE. Formalin-fixed kidney sections of rats from each treatment group at 32 weeks were mounted on slides and stained with 6D12 monoclonal anti-AGE antibodies specific for CML.

FIG. 14 shows immunohistochemical staining for nitrotyrosine. Formalin-fixed kidney sections of rats from each treatment group at 32 weeks were mounted on slides and stained anti-nitrotyrosine polyclonal antibodies.

FIG. 18 shows the effects of diabetes and LR treatment on renal CML-AGE accumulation. Magnification 200x.

FIG. 22 is a series of photographs showing the effect of diabetes and LR compounds on renal protein oxidation. (FIG. 22A): non-diabetic control; (FIG. 22B): diabetic control; (FIG. 22C): diabetic plus LR-9; (FIG. 22D): diabetic plus LR-74. Magnification is 200x.

DETAILED DESCRIPTION OF THE PREFERRED EMBODIMENTS

Figure 1:
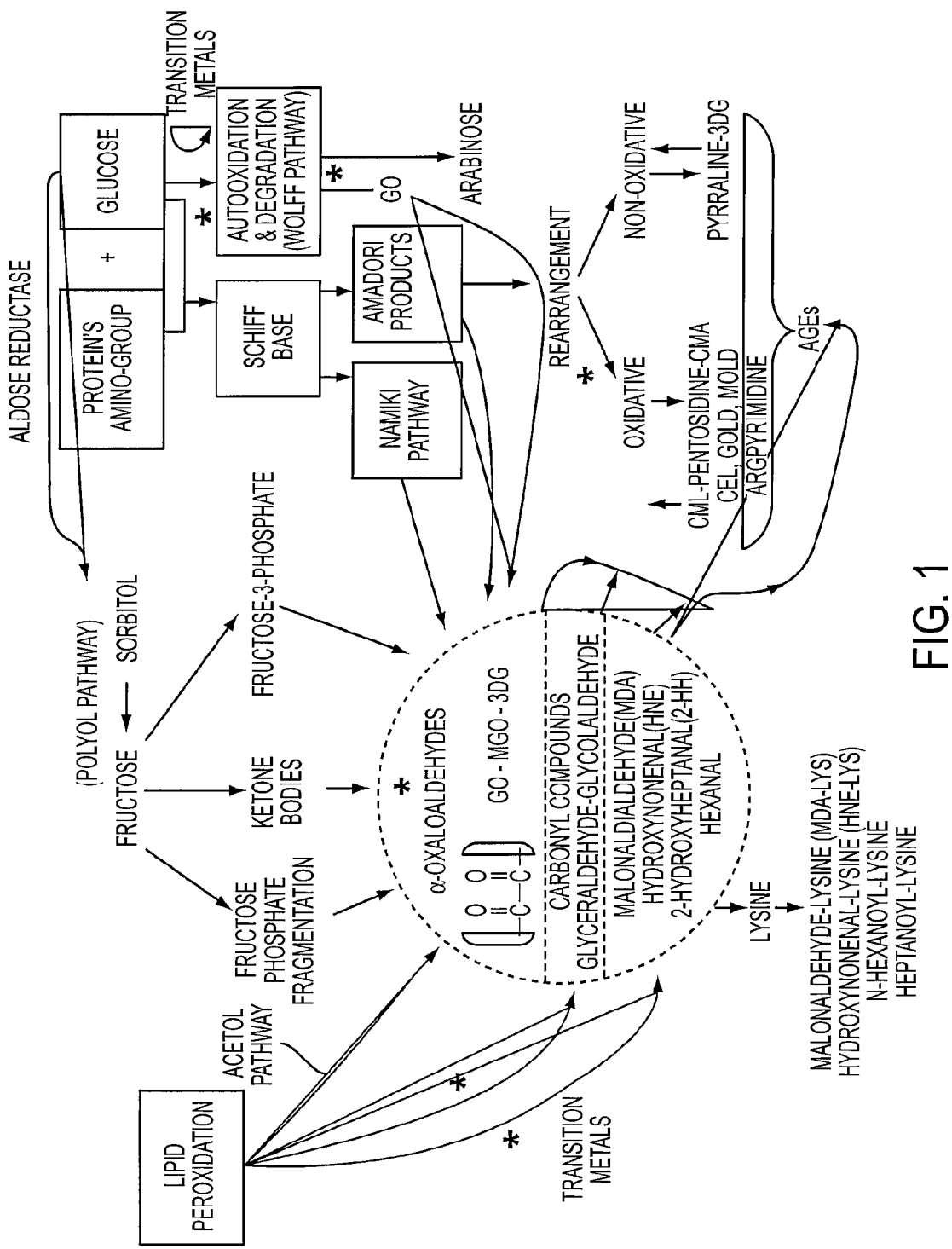
FIG. 1 is a diagram showing metabolic sources of reactive carbonyl species and carbonyl stress. Asterisks in the diagram represent the postulated pathways where the LR compounds exert their effects.
Figure 2:
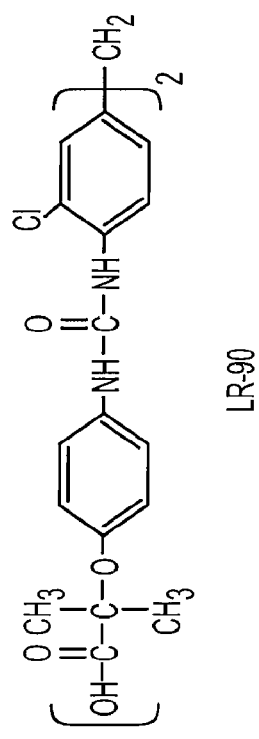
FIG. 2 shows the chemical structures of compounds LR-9 [4-(2-napthylcarboxamido) phenoxyisobutyric acid]; LR-74 [2-(8-quinolinoxy) propionic acid]; and LR-90 [methylene bis (4,4'-(2-chlorophenylureidophenoxyisobutyric acid)].
Figure 2:
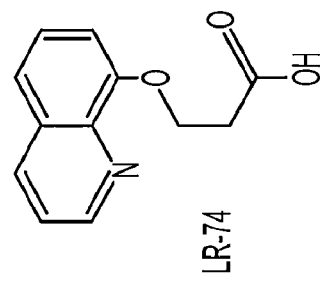
Figure 2:
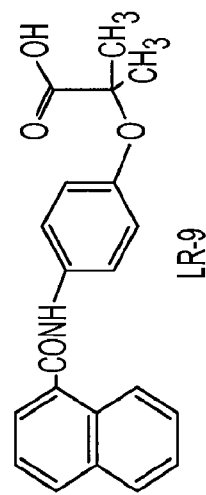

The LR compounds discussed here (see FIG. 2) belong to a group of novel aromatic compounds derived from LR-16.

LR-16 acts as an allosteric effector, synergistic with 2,3-bisphosphoglycerate in increasing the oxygen affinity of hemoglobin molecules, and which has been shown to lower serum cholesterol and low-density lipoproteins (LDL) in rats which were fed a diet rich in cholesterol. Lalezari et al., *Proc. Natl. Acad. Sci. USA* 85:6117-6121, 1988.

The studies presented here showed that diabetic rats treated with any of the new LR compounds provided statistically significant improvement in renal function in terms of development of proteinuria and reduction in creatinine excretion. In addition, histochemical observations showed that treatment with these LR compounds minimized kidney structural damage as indicated by a reduction in the incidence of glomerulosclerosis, cortical tubule degeneration and collagen deposition in the kidney compared to untreated diabetic rats. Additionally, the compounds prevented mesangial expansion and basement membrane thickening of the kidneys of diabetic rats. These compounds effectively inhibited the increase in serum AGE and the in situ accumulation of immunoreactive AGEs in collagen tissues and kidneys of diabetic rats without any effect on hyperglycemia. The LR compounds lowered cholesterol and triglyceride concentrations found in the hyperlipidemia of diabetic rats but did not significantly change in the lipid levels of control non-diabetic rats.

Without wishing to be bound by theory, two proposed mechanisms for the beneficial effects of the LR compounds in preventing diabetic nephropathy, are their lipid lowering activities per se, or their AGE inhibitor and antioxidative properties. Reduction of plasma lipids by treatment with lipid lowering compounds such as statins has been shown to provide protection against nephropathy in non-diabetic obese rats. O'Donnell et al., *Am. J. Kidney Dis.* 22:83-89, 1993; Oda and Keane, *Kidney Int. Suppl.* 71:S2-S5, 1999. On the other hand, the AGE/ALE inhibitor pyridoxamine have been also shown to correct hyperlipidemia and nephropathy in both diabetic rats and non-diabetic rats obese rats, probably by interfering with various reactive carbonyl intermediates of AGE/ALE formation from lipid oxidation. Degenhardt et al., *Kidney Int.* 61:939-950, 2002; Alderson et al., *Kidney Int.* 63:2123-2133, 2003. Unlike pyridoxamine, which has minimal effects on lipid peroxidation, all three LR compounds were strong inhibitors of LDL oxidation in vitro.

Thus, in addition to its protective effects on kidneys in diabetic rats, these novel compounds can be used in the treatment of atherosclerosis and other vascular complications of diabetes. Such additional beneficial effects were unexpected. Although there was the possibility that the increased lipid peroxidation seen in the diabetic rats is correlated with the higher substrate levels (increased plasma lipid levels) in these animals relative to non-diabetic rats, there was no significant correlation between plasma cholesterol or triglyceride concentration and the levels of plasma lipid hydroperoxides in both non-diabetic and diabetic control rats. These results suggest that lipid peroxidation may be independent of the total available lipids in the plasma, which is consistent with earlier observations in human and animal studies. Griesmacher et al., *Am. J. Med.* 98:469-475, 1995; Ihm et al., *Metabolism* 48:1141-1145, 1999. More importantly, these findings indicate that the elevated lipid peroxidation products could be associated with increased oxidative stress as a consequence of increased AGE/ALE formation in the diabetic rats.

Known AGE inhibitors with renoprotective effects such aminoguanidine, pyridoxamine, and OPB-9195 are thought to prevent AGE/ALE accumulation by interacting with highly reactive RCS and acting as carbonyl traps, preventing AGE/ALE formation. However, the metal chelation properties of these AGE inhibitors may contribute to their effectiveness in preventing AGE formation in vivo. The mechanism of action of these LR compounds is still unclear, but the LR compounds are potent chelators of $Cu^{2+}$, (more potent than AG and PM), and are effective inhibitors of oxidation of ascorbic acid. Moreover, these compounds strongly inhibit hydroxyl radical formation, and LR-90 also may prevent superoxide production. The various pathways involved in the production and generation of protein carbonyls and Amadori products important in the formation of some AGEs and ALEs may require free radicals, transition metals, or both. Miyata et al., *J. Am. So. Nephrol.* 13:2478-2487, 2002; Voziyan et al., *J. Biol. Chem.* (2003 Sep. 15) [Epub ahead of print]. However, unlike aminoguanidine and pyridoxamine which act primarily by trapping RCS, these novel LR compounds also reduce the production of RCS by interfering with oxidative metabolism, for example by lowering formation of hydroxyl radicals and interacting with metal ions that can further promote sugar/lipid oxidation reactions.

Notably, the compounds LR-9, -74 and -90 are potent inhibitors of the copper catalyzed oxidation of ascorbic acid. This observation points to several additional uses of LR-9, -74 or -90, including as therapeutics in conditions, syndromes or diseases involving copper. In the body, copper ions can be found in the cuprous ($Cu^+$) or the cupric ($Cu^{++}$) states. In general, diseases involving copper fall into two main categories: (1) diseases involving environmental exposure to copper, including excess levels of copper and (2) diseases involving copper metabolism, the distribution of copper within the body and the role of copper in biological processes, including the involvement of copper in enzymes or biological processes. Some copper-related enzymes implicated in disease include: superoxide dismutase (Cu/Zn SOD) (implicated in amyothrophic lateral sclerosis); tyrosine hydroxylase and dopamine-beta-hydroxylase that form or catabolize several brain neurotransmitters such as dopamine and norepinephrine; monoamine oxidase (MAO) which plays a role in the metabolism of the neurotransmitters norepinephrine, epinephrine, and dopamine and also functions in the degradation of the neurotransmitter serotonin; lysyl oxidase which is required for the cross-linking of collagen and elastin; and cytochrome c oxidase which is involved in the synthesis of phospholipids which comprise structures such as the myelin sheath of neurons.

Ceruloplasmin, a copper binding protein, is thought to prevent free copper ions from catalyzing oxidative damage. Ceruloplasmin has ferroxidase activity (oxidation of ferrous iron) which facilitates iron loading onto its transport protein. This transfer may prevent free ferrous ions ($Fe^{2+}$) from promoting the generation of free radicals. Thus, the level of serum copper and/or the copper-loading status of ceruloplasmin may modulate iron metabolism. Copper-dependent transcription factors may affect the transcription of specific genes including genes for Cu/Zn SOD, catalase (another antioxidant enzyme), and proteins related to the cellular storage of copper. Further specific disease conditions involving copper metabolism include Menkes Disease (also known as Menkes Kinky Hair Syndrome), Wilson's Disease and X-linked Cutis Laxa (also known as type IX Ehlers-Danlos syndrome or Occipital Horn syndrome) listed via OMIN reference numbers #309400, #277900, and #304150 respectively. The particular symptoms seen in these conditions (for example, osteoporosis, neurodegeneration in the gray matter of the brain damaged cerebral arteries leading to vascular rupture or blockage in Menkes patient) may indicate more general roles for copper in such symptoms or disease processes such as cerebrovascular infarction, vascular rupture, etc.

Thus, copper plays a broad role in a number of biological pathways present in normal or disease states where therapeutic intervention using compounds that modulate copper would be advantageous. The desirable activities of such compounds may include, but may not be limited to chelation of free copper in solution, mobilization of copper from carrier proteins, optimal distribution of copper into the preferred biological compartment, the optimal sequestration of copper into biological compartments and/or the promotion of copper excretion.

The effective dosages and modes of administration are made in accordance with accepted medical practices taking into account the clinical condition of the individual subject (e.g. severity and course of the disease), the site and method of administration, scheduling of administration, patient age, sex, body weight and other factors known to medical practitioners. Accordingly, the dosages of the compositions of the invention for treatment of a subject are to be titrated to the individual subject. For example, the interrelationship of dosages for animals of various sizes and species and humans based on mg/m$^2$ of surface area is described by Freireich et al., *Cancer Chemother. Rep.* 50(4):219-244 (1966). The "effective dose" can be determined by procedures known in the art, and must be such as to achieve a discernible change in the disease state.

In addition to their effects on AGE formation and lipid metabolism, LR treatment also may influence some steps in the inflammation pathways leading to tissue injury. LR-90 also prevented cell infiltration in the renal interstitium of diabetic rats. In fact, no neutrophils were detected in LR-90 treated diabetic rats, which were numerous and in dense aggregates in untreated diabetic rats, important because CML formation at the site of tissue injury is promoted by enzymatic catalysis by neutrophils. Activated neutrophils use myeloperoxidase-hydrogen peroxide-chloride system to convert hydroxy-amino acids into GLA and other reactive aldehydes which are precursors for CML. Anderson et al., *J. Clin. Invest.* 104:103-113, 1999. Such in vivo production of CML precursors could play a major role in the renal pathology observed here by generating additional AGE production at the site of injury since CML adducts of proteins are ligands for AGE that activate cell signaling pathway and modulate gene expression. In vitro and in vivo studies indicate that CML and other AGE can enhance formation of reactive oxygen species and induce NF-κB activation in proximal endothelial cells, perpetuating an increase in proinflammatory gene products, cytokines, adhesion molecules, and ROS that all can contribute to renal damage. Morcos et al., *Diabetes* 51:3532-3544, 2002; Boulanger et al., *Kidney Int.* 61:148-156, 2002; Basta et al., *Circulation* 105:816-822, 2002.

LR-90 treatment decreased the overall oxidative damage to renal tissues, as shown by nitrotyrosine formation in renal cortex. Recent studies indicate that increased nitrotyrosine concentrations play a major role in early diabetic tubular damage and in the progression of renal disease. Thuraisingham et al., *Kidney Int.* 57:968-972, 2002. Proximal tubular cells produce nitric oxide (NO), which can react with superoxide to form peroxynitrite (ONOO$^-$), a powerful oxidant. Peroxynitrite nitrosylates tyrosine moieties on proteins, producing nitrotyrosine. Beckman and Koppenol, *Am. J. Physiol.* 271 (5 Pt 1): C1424-C1437, 1996; Reiter et al., *J. Biol. Chem.* 275:32460-32466, 2000. In vitro studies have suggested that glycation itself can result in the production of superoxide and hydroxyl radicals through transition metal. Sakurai et al., *FEBS Lett.* 236:406-410, 1988; Yim et al., *J. Biol. Chem.* 270:28228-28233, 1995; Ortwerth et al., *Biochem. Biophys. Res. Commun.* 245:161-165, 1998. The increase in CML-AGE and nitrotyrosine staining in rats with diabetic nephropathy can be attenuated by ramipril and aminoguanidine, indicating that ACE inhibition and blockage of AGE formation could involve common pathways such as ROS formation. Forbes et al., *Diabetes* 51:3274-3282, 2002.

AGE/ALE formation can stimulate the oxidation of lipids by generation of oxidizing intermediates, including free radicals, in the presence of trace amounts of iron or copper which act as catalysts. Formation of free radicals is enhanced in diabetes by glucose oxidation (glycoxidation), non-enzymatic glycation of proteins, oxidative decomposition of glycated proteins, and interaction of AGEs/ALEs with RAGE. Abnormally high levels of free radicals and the simultaneous decline in antioxidant defense mechanisms may lead to increased oxidative stress and subsequent lipid peroxidation. As shown in the present study, diabetic animals exhibited higher levels of oxidative stress in both kidneys and plasma as indicated by enhanced nitrotyrosine staining in the kidney tubules and glomeruli, and increased lipid hydroperoxides in plasma. Evidence in both experimental and clinical studies suggests that hyperglycaemia-induced oxidative stress can play a major role in the lipid metabolism in diabetes.

Both glucose oxidation and glycation can catalyze PUFA peroxidation of cell membranes. In high glucose-environment, proteins and lipoproteins trapped within tissues can undergo glycation to produce ROS and lipid peroxidation products. However, based on the results of this study untreated and LR-treated diabetic rats showed no difference in glucose and HbAlc concentration, indicating that hyperglycaemia alone might have only limited influence the levels of lipid peroxidation. In contrast, there were significant differences in the levels of AGE/ALE in collagen and in kidneys of untreated and LR-treated diabetic animals, concomitant with decreased concentrations of lipids and lipid peroxidation products after LR treatment. Taken together, these data suggest that inhibition of AGEs/ALEs formation can prevent oxidative stress and subsequent damage in diabetic animals.

Recent studies with the AGE/ALE inhibitor PM in normoglycemic Zucker obese and hyperlipemic rats have raised some interesting questions about whether lipids and ALEs, and not carbohydrates and AGEs, are responsible for most of chemical modifications and tissue damage in diabetes Mert et al., *J. Biol. Chem.* 278:42012-42019, 2003; Januszewski et al., *Biochem. Soc. Trans. B*1: 1413-1415, 2003; Alderson et al., *Kidney Int.* 63: 2123-2133, 2003. Oxidative stress in these rats can trigger the onset of kidney lesions and renal dysfunction, concurrent with the first appearance of lipid peroxidation products and decline of antioxidant enzyme activities. See Poirier et al., *Nephrol. Dial. Transplant.* 15: 467-476, 2000. Overall, these studies suggest that hyperlipidaemia and lipid peroxidation can independently induce renal impairment in the absence of hyperglycaemia. Additionally, both hypercholesterolemia and hypertriglyceridaemia are recognized as independent risk factors for the development of renal disease and are also associated with nephrotic syndromes independent of diabetes. Furthermore reduction of plasma lipids by lipid lowering drugs (e.g., statins) have successfully resulted in renoprotection against diabetic nephropathy. As documented in this study, LR-9 and LR-74 inhibit lipid peroxidation reactions, and therefore possess general antioxidant properties. Both these compounds have weaker carbonyl trapping activities compared with AG, PM and LR-90, but are strong inhibitors of hydroxyl radicals formation, and consequently may be working on a different AGE/ALE inhibition mechanism compared with these prototype AGE inhibitors.

Oxygen, redox active transition metals and ROS are catalysts of AGE and ALE formation. The various pathways involved in the production and generation of RCS and Amadori products, important in the formation of some AGEs and ALEs, thus may require free radicals, transition metals, or both. However, unlike AG and PM, which act primarily by trapping RCS, the LR compounds discussed here also may reduce the product of RCS by interfering with oxidative metabolism, probably by inhibiting formation of free radicals and interacting with metal ions that can further promote sugar/lipid oxidation reactions. Here, LR compounds reduced the levels of AGEs/ALEs such as CML and CEL, inhibited the chemical modifications of collagens, and decreased the overall oxidative stress in plasma and kidneys of diabetic animals. All these effects can influence the thickening and loss of elasticity of the vascular wall, membrane permeability, and inflammatory process (via RAGE interaction), which can lead to the prevention of dyslipidaemia.

Regardless of how the LR compounds lower plasma lipids and inhibit lipid peroxidation reactions in vivo, such effects further broaden the possible therapeutic applications of these compounds. Decomposition of lipid peroxides initiates chain of reactions that produce various RCS that can generate AGEs and ALEs and various lipid adducts which can lead to the accumulation of lipids and lipoproteins in form cells in vascular wall. LDL has been identified as the major carrier of lipid hydroperoxides in the plasma and oxidative modification of LDL has been suggested as a causal step in the development of atherosclerosis. Redox-active transition metals and fee radicals, as well as AGE formation and glycoxidation, have been implicated in this process. While there is conflicting evidence for the actual involvement of transition metals in modifying LDL in vivo, human atherosclerotic lesions contain elevated levels of redox-active copper and iron, and various antioxidants have been shown to inhibit LDL oxidation and retard the development of atherosclerosis in human and animal models. Metal chelation therapy is effective in improving endothelial function in patients with coronary artery disease. Thus agents that can inhibit AGE/ALE formation and reduce the oxidative stress are in a position to prevent the development of atherosclerosis in diabetic subjects. The ability of LR compounds to chelate copper in this study could be one of the mechanisms for the observed inhibition of lipid peroxidation reactions in vitro and in vivo, since no adducts formed between the fatty acid (linoleic acid) and the compounds were detected using RP-HPLC, and these compounds were not consumed in the lipoxidation reaction. In addition, neither compound had any effect of lipoxygenase-mediated LDL oxidation. These findings further reinforce the showing that these LP compounds inhibit AGE/ALE formation, and at least to some extent lipid peroxidation reactions, mainly through their antioxidant/metal chelation properties. The overall superior renoprotective, lipid-lowering and anti-lipid peroxidation effects of LR-74 relative to LR-9 in the present study could be a reflection of the better antioxidant and hydroxyl radical scavenger characteristics of the former compound Figarola et al., *Diabetologia* 46:1140-1152. However, while both drugs were given at 50 mg/L, LR-74 was administered at about 1½ times the LR-9 dose (about 0.15 mmol/L for LR-9 vs. 0.23 mmol/L for LR-74). Assuming similar bioavailability and pharmacokinetics, the effects of LR-9 are as impressive as LR-74 despite these differences in dosages administered in animals.

In summary, we have identified compounds that can inhibit AGE/ALE formation in vivo and also delay or inhibit the progression of early renal dysfunction in diabetic animals. These compounds also prevent hyperlipidaemia and inhibit the overall oxidative stress in these animals. The LR compounds described here can be an effective treatment modality for early renal disease and other diabetic complications where accumulation of AGEs/ALEs and intermediate compounds are primary contributors. Aside from their AGE inhibitory properties, these compounds possess lipid-lowering characteristics that can influence both the development of diabetic renal disease and atherosclerosis. The ability of the compounds to chelate transition metals, their interaction with RCS and/or intervention with RCS formation, as well as inhibiting free radical production, could be mediating the renoprotective and lipid-lowering effects of these compounds.

REFERENCES

1. Abrass, Cellular lipid metabolism and the role of lipids in progressive renal disease. *Am. J. Nephrol.* 24:46-53, 2004.
2. Al-Abed et al., Advanced glycation end products: detection and reversal. *Methods Enzymol.* 309:152-172, 1999.
3. Alderson et al., The AGE inhibitor pyridoxamine inhibits lipemia and development of renal and vascular disease in Zucker obese rats. *Kidney Int.* 63:2123-2133, 2003.
4. Altomare et al., Increased lipid peroxidation in type 2 poorly controlled diabetic patients. *Diabetes Metab.* 18:264-271, 1992.
5. Anderson et al., The myeloperoxidase system of human phagocytes generates N-epsilon(carboxymethyl)lysine on proteins: a mechanism for producing advanced glycation end products at sites of inflammation. *J. Clin. Invest.* 104: 103-113, 1999.
6. Basta et al., Advanced glycation end products activate endothelium through signal-transduction receptor RAGE: a mechanism for amplification of inflammatory responses. *Circulation* 105:816-822, 2002.
7. Baynes and Thorpe, Perspective in diabetes: role of oxidative stress in diabetes complications. A new perspective on an old paradigm. *Diabetes* 48:1-9, 1999.
8. Baynes and Thorpe, Glycoxidation and lipoxidation in atherogenesis. *Free Rad. Biol. Med.* 28:1708-1716, 2000.
9. Beckman and Koppenol, Nitric oxide, superoxide, and peroxynitrite: the good, the bad, and ugly. *Am. J. Physiol.* 271 (5 Pt 1):C1424-C1437, 1996.
10. Boel et al., Diabetic late complications: will aldose reductase inhibitors or inhibitors of advanced glycosylation endproduct formation hold promise? *J. Diabetes Complications* 9:104-129, 1995.
11. Boulanger et al., AGEs bind to mesothelial cells via RAGE and stimulate VCAM-1 expression. *Kidney Int.* 61:148-156, 2002.
12. Browlee, Biochemistry and molecular cell biology of diabetic complications. *Nature* 414:813-820, 2001.
13. Bucala et al., Modification of DNA by reducing sugars: a possible mechanism for nucleic acid aging and age-related dysfunction in gene expression. *Proc. Natl. Acad. Sci. USA* 81: 105-109, 1984.
14. Bucala and Cerami, Advanced glycosylation: chemistry, biology and implications for diabetes and aging. *Adv. Pharmacol.* 23:1-33, 1992.
15. Bucala et al., Lipid advanced glycation pathway for lipid oxidation. *Proc. Natl. Acad. Sci. USA* 90:6434-6438, 1993.
16. Bucala and Vlassara, Lipid and lipoprotein modification by advanced glycation end-products: Role in atherosclerosis. *Exper. Physiol.* 82:327-337, 1997.
17. Bucala and Rahbar, Protein glycation and vascular disease. In: *Endocrinology of cardiovascular function*. E. R. Levin and J. L. Nadler (eds.). (1998) Kluwer Acad. Publishers, pp. 159-180.

18. Carew et al., Antiatherogenic effect of probucol unrelated to its hypocholesterolemic effect: evidence that antioxidants in vivo can selectively inhibit low density lipoprotein degradation in macrophage-rich fatty streaks and slow the progression of atherosclerosis in the Watanabe heritable hyperlipidemic rabbit. *Proc. Natl. Acad. Sci. USA* 84:7725-7729, 1987.
19. Carpenter et al., Oral alpha-tocopherol supplementation inhibits lipid oxidation in established human atherosclerotic lesions. *Free Radic. Res.* 37:1235-1244, 2003.
20. Chaturvedi et al., Microalbuminuria in type 1 diabetes: rates, risk factors and glycemic threshold. *Kidney Int.* 60:219-227, 2001.
21. Chellan and Nagaraj, Protein crosslinking by the Maillard reaction: dicarbonyl-derived imidazolium crosslinks in aging and diabetes. *Arch. Biochem. Biophys.* 368:98-104, 1999.
22. Chung et al., Single vertical spin density gradient ultracentrifugation. *Methods Enzymol.* 128:181-209, 1978.
23. Creemers et al., Microassay for the assessment of low levels of hydroxyproline. *Biotechniques* 22:656-658, 1997.
24. Degenhardt et al., Pyridoxamine inhibits early renal disease and dyslipidemia in the streptozotocin-diabetic rat. *Kidney Int.* 61:939-950, 2002.
25. The Diabetes Control and Complications Trial Research Group (1993). The effect of intensive treatment of diabetes on the development and progression of long-term complications in insulin-dependent diabetes mellitus. #*N. Engl. J. Med.* 329:977-986, 1993.
26. Dillon et al., Antioxidant properties of aged garlic extract: an in vitro study incorporating human low density lipoprotein. *Life Sci.* 72:1583-1594, 2003.
27. Duffy et al., Iron chelation improves endothelial function in patients with coronary artery disease. *Circulation* 103: 2799-2804, 2001.
28. Esterbauer et al., Chemistry and biochemistry of 4-hydroxynonenal, malonaldehyde and related aldehydes. *Free Radic. Biol. Med.* 11:81-128, 1991.
29. Figarola et al., LR-90, a new advanced glycation endproduct inhibitor prevents progression of diabetic nephropathy in STZ-diabetic rats. *Diabetologia* 46:1140-1152, 2003.
30. Forbes et al., Reduction of the accumulation of advanced glycation end products by ACE inhibition in experimental diabetic nephropathy. *Diabetes* 51:3274-3282, 2002.
31. Friedman, Advanced glycation end-products in diabetic nephropathy. *Nephrol. Dial. Transplant.* 14 (Suppl 3):1-9, 1999.
32. Fu et al., The advanced glycation end product, $N^\epsilon$-(carboxymethyl)lysine, is a product of both lipid peroxidation and glycoxidation reactions. *J. Biol. Chem.* 271:9982-9986, 1996.
33. Giardino et al., Aminoguanidine inhibits reactive oxygen species formation, lipid peroxidation, and oxidant-induced apoptosis. *Diabetes* 47:1114-1120, 1998.
34. Gogasyavuz et al., Effects of aminoguanidine on lipid and protein oxidation in diabetic rat kidneys. *Int. J. Exp. Diabetes Res.* 3:145-151, 2002.
35. Griesmacher et al., Enhanced serum levels of thiobarbituric-acid-reactive substances in diabetes. *Am. J. Med.* 98:469-475, 1995.
36. Heinecke, Oxidants and antioxidants in the pathogenesis of atherosclerosis: implications for the oxidized low density lipoprotein hypothesis. *Atherosclerosis* 141:1-15, 1998.
37. Hendrick et al., Glycation impairs high-density lipoprotein function. *Diabetologia* 43:312-320, 2000.
38. Hicks et al., Catalysis of lipid peroxidation by glucose and glycosylated collagen. *Biochem. Biophys. Res. Commun.* 151:649-655, 1988.
39. Horie et al., Immunohistochemical colocalization of glyoxidation products and lipid peroxidation products in diabetic renal glomerular lesions. *J. Clin. Invest.* 100:2995-3004, 1997.
40. Ihm et al., Effect of aminoguanidine on lipid peroxidation in streptozotocin-induced diabetic rats. *Metabolism* 48:1141-1145, 1999.
41. Inouye et al., Glycated hemoglobin and lipid peroxidation in erythrocytes of diabetic patients. *Metabolism* 48:205-209, 1999.
43. Jain et al., Erythrocyte membrane lipid peroxidation and glycosylated hemoglobin in diabetes. *Diabetes* 38:1539-1543, 1989.
44. Januszewski et al., Role of lipids in chemical modification of proteins and development of complications in diabetes. *Biochem. Soc. Trans.* 31:1413-1416, 2003.
45. Jenkins et al., Lipoproteins in the DCCT/EDIC cohort: associations with diabetic nephropathy. *Kidney Int.* 64:817-828, 2003.
46. Joles et al., Early mechanisms of renal injury in hypercholesterolemic or hypertriglyceridemic rat. *J. Am. Soc. Nephrol.* 11:669-683, 2000.
47. Kawamura et al., Pathophysiological concentrations of glucose promotes oxidative modification of low density lipoprotein by a superoxide-dependent pathway. *J. Clin. Invest.* 942:771-778, 1994.
48. Kennedy and Lyons, Glycation, oxidation, and lipoxidation in the development of diabetic complications. *Metabolism* 46:14-21, 1997.
49. Kislinger et al., N(epsilon)-(carboxymethyl)lysine adducts of proteins are ligands for receptor for advanced glycation end products that activate cell signaling pathways and modulate gene expression. *J. Biol. Chem.* 274:31740-3174, 1999.
50. Knott et al., Glycation and glycoxidation of low-density lipoproteins by glucose and low-molecular mass aldehydes. Formation of modified and oxidized particles. *Eur. J. Biochem.* 270:3572-3582, 2003.
51. Kochakian et al., Chronic dosing with aminoguanidine and novel advanced glycosylation end product-formation inhibitors ameliorates cross-linking of tail tendon collagen in STZ-induced diabetic rats. *Diabetes* 45:1694-1700, 1996.
52. Kushiro et al., Accumulation of N sigma-(carboxy-methyl)lysine and changes in glomerular extracellular matrix components in Otsuka Long-Evans Tokushima fatty rat: a model of spontaneous NIDDM. *Nephron* 79:458-468, 1998.
53. Lalezari et al., LR16, a compound with potent effects on the oxygen affinity of hemoglobin, on blood cholesterol, and on low density lipoprotein. *Proc. Natl. Acad. Sci. USA* 85:6117-6121, 1988.
54. Lam et al., Cholesterol-lowering therapy may retard the progression of diabetic nephropathy. *Diabetologia* 38:604-609, 1995.
55. Lamb et al., Transistion metal ions within human atherosclerotic lesions can catalyse the oxidation of low-density lipoprotein by macrophages. *FEBS Lett.* 374:12-16, 1995.
56. Lo et al., The reaction of methylglyoxal with aminoguanidine under physiological conditions and prevention of methylglyoxal binding to plasma proteins. *Biochem. Pharmacol.* 48:1865-1870, 1994.
57. Lopes-Virella et al., Modification of lipoprotein in diabetes. *Diabetes Metab. Rev.* 12:69-90, 1996.

58. Lyons et al., Glycation, oxidation and lipoxidation in the development of the complications of diabetes mellitus: a 'carbonyl stress' hypothesis. *Diabetes Rev.* 5:365-391, 1997.
59. Makita et al., Advanced glycosylation end products in patients with diabetic nephropathy. *N. Eng. J. Med.* 325:836-842, 1993.
60. Matsumoto et al., Immunohistochemical evidence for increased formation of advanced glycation end products and inhibition by aminoguanidine in diabetic rat lines. *Biochem. Biophys. Res. Commun.* 241:352-354, 1997.
61. Metz et al., Pyridoxamine, an inhibitor of advanced glycation and lipoxidation reactions: a novel therapy for treatment of diabetic complications. *Arch. Biochem. Biophys.* 419:41-49.
62. Metz et al., Pyridoxamine traps intermediates in lipid peroxidation reactions in vivo: evidence on the role of lipids in chemical modification of protein and development of diabetic complications. *J. Biol. Chem.* 278:42012-42019, 2003.
63. Miyata et al., Generation of protein carbonyls by glycoxidation and lipoxidation reactions with autoxidation products of ascorbic acid and polyunsaturated fatty acids. *FEBS Lett.* 437:24-28, 1993.
64. Miyata et al., Advanced glycation and lipoxidation end products: role of reactive carbonyl compounds generated during carbohydrate and lipid metabolism. *J. Am. Soc. Nephrol.* 11:1744-1752, 2000.
65. Miyata et al., Angiotensin II receptor antagonists and angiotensin-converting enzyme inhibitors lower in vitro the formation of advanced glycation end products: biochemical mechanisms. *J. Am. So. Nephrol.* 13:2478-2487, 2002.
66. Miyata et al., Angiotensin II receptor blockers and angiotensin converting enzyme inhibitors: implication of radical scavenging and transition metal chelation in inhibition of advanced glycation end product formation. *Arch. Biochem. Biophys.* 419:50-54, 2003.
67. Morcos et al., Activation of tubular epithelial cells in diabetic nephropathy. *Diabetes* 51:3532-3544, 2002.
68. Mowri et al., Glucose enhancement of LDL oxidation is strictly metal ion dependent. *Free Radic. Biol. Med.* 29:814-824, 2000.
69. Mullarkey et al., Free radical generation by early glycation products: a mechanism for accelerated atherogenesis in diabetes. *Biochem. Biophys. Res. Commun.* 173:771-778, 1994.
70. Muntner et al., Plasma lipids and risk of developing renal dysfunction: the atherosclerosis risk in communities study. *Kidney Int.* 58:293-301, 2000.
71. Nagaraj et al., Effects of pyridoxamine on chemical modifications of proteins by carbonyls in diabetic rats: characterization of a major product from the reaction of pyridoxamine with methylglyoxal. *Arch. Biochem. Biophys.* 402:110-119, 2002.
72. Nourooz-Zadeh et al., Low-density lipoprotein is the major carrier of lipid hydroperoxides in plasma. Relevance to determination of total plasma lipid hydroperoxide concentrations. *Biochem. J.* 313:781-786, 1996.
73. Nangaku et al., Anti-hypertensive agents inhibit in vivo the formation of advanced glycation end products and improve renal damage in a type 2 diabetic nephropathy rat model. *J. Am. Soc. Nephrol.* 14:1212-1222, 2003.
74. Oda and Keane, Recent advances in statins and the kidney. *Kidney Int. Suppl.* 71:S2-S5, 1999.
75. O'Donnell et al., Lovastatin retards the progression of established glomerular disease in obese Zucker rats. *Am. J. Kidney Dis.* 22:83-89, 1993.
76. Ortwerth et al., The generation of superoxide anions in glycation reactions with sugars, osones, and 3-deoxyosones. *Biochem. Biophys. Res. Commun.* 245:161-165, 1998.
77. Poirier et al., Oxidative stress occurs in absence of hyperglycaemia and inflammation in the onset of kidney lesions in normotensive obese rats. *Nephrol. Dial. Transplant.* 15:467-476, 2000.
78. Price et al., Chelating activity of advanced glycation end-products inhibitors. *J. Biol. Chem.* 276:48967-48972, 2001.
79. Rahbar et al., Novel inhibitors of glycation endproducts. *Biochem. Biophys. Res. Commun.* 262:651-656, 1999.
80. Rahbar et al., Novel inhibitors of advanced glycation endproducts (Part II). *Mol. Cell. Biol. Res. Comm.* 3:360-366, 2000.
81. Rahbar and Figarola, Inhibitors and breakers of advanced glycation endproducts (AGEs): a review. *Curr. Med. Chem.-Immunol. Endocr. Metabol. Agents* 2:135-161, 2002.
82. Rahbar and Figarola, Inhibitors and breakers of advanced glycation endproducts. *Curr. Med. Chem.-Immunol. Endocrin. Metabol.* 2: 174-186, 2002.
83. Rahbar and Figarola, Novel inhibitors of advanced glycation endproducts. *Arch. Biochem. Biophys.* 419:63-79, 2003.
84. Reiter et al., Superoxide reacts with nitric oxide to nitrate tyrosine at physiological pH via peroxynitrite. *J. Biol. Chem.* 275:32460-32466, 2000.
85. Requena et al., Lipoxidation products as biomarkers of oxidative damage to proteins during lipid peroxidation reactions. *Nephrol. Dial. Transplant.* 11 (Suppl 5):48-53, 1996.
86. Requena et al., Carboxymethylethanolamine: a biomarker of phospholipid modification during the Maillard reaction in vivo. *J. Biol. Chem.* 272:17473-14779, 1997.
87. Sakata et al., Glycoxidation and lipid peroxidation of low-density lipoprotein can synergistically enhance atherogenesis. *Cardiovasc. Res.* 49:466-475, 2001.
88. Sakurai and Tsuchiya, Superoxide production from non-enzymatically glycated protein. *FEBS Lett.* 236:406-410, 1988.
89. Satoh, Serum lipid peroxide in cerebrovascular disorders determined by a new colorimetric method. *Clin. Chim. Acta* 90:37-43, 1978.
90. Shaw et al., N-epsilon-(carboxymethyl)lysine (CML) as a biomarker of oxidative stress in long-lived tissue proteins. *Methods Mol. Biol.* 186:129-137, 2002.
91. Sheetz and King, Molecular understanding of hyperglycemia's adverse effects for diabetic complications. *JAMA* 288: 2579-2588, 2002.
92. Singh et al., Advanced glycation end-products: a review. *Diabetologia* 44:129-146, 2001.
93. Slatter et al., The importance of lipid-derived malondialdehyde in diabetes mellitus. *Diabetologia* 43:550-557, 2000.
94. Smith et al., Stimulation of lipid peroxidation and hydroxyl-radical generation by the contents of human atherosclerotic lesions. *Biochem. J.* 286:901-905, 1992.
95. Stadler et al., Direct detection and quanification of transition metal ions in human atherosclerotic plaques: evidence for the presence of elevated levels of iron and copper. *Arterioscler. Thromb. Vasc. Biol.* 24:949-954, 2004.

96. Stefek et al., p-Dimethyl aminobenzaldehyde-reactive substances in tail tendon collagen of streptozotocin-diabetic rats: temporal relation to biomechanical properties and advanced glycation endproduct (AGE)-related fluorescence. *Biochim. Biophys. Acta* 1502:398-404, 2000.
97. Stith et al., Advanced glycation end products and diabetic complications. *Expert Opin. Invest. Drugs* 11:1205-1223, 2002.
98. Teuscher et al., Nephropathy subsequent to hyperlipidemia. *Clin. Nephrol.* 54:64-67, 2000.
99. Thornalley et al., Formation of glyoxal, methylglyoxal and 3-deoxyglucosone in the glycation of proteins by glucose. *Biochem. J.* 344:109-116, 1999.
100. Thornalley et al., Kinetics and mechanism of the reaction of aminoguanidine with the alpha-oxoaldehydes glyoxal, methylglyoxal, and 3-deoxyglucosone under physiological conditions. *Biochem. Pharmacol.* 60:55-65, 2000.
101. Thorpe and Baynes, Role of oxidative stress in development of complications in diabetes: a new perspective on an old paradigm. *Diabetes* 48:1-9, 1999.
102. Thorpe and Baynes, Maillard reaction products in tissue proteins: new products and new perspectives. *Amino Acids* 25:275-281, 2002.
103. Thuraisingham et al., Increased nitrotyrosine staining in kidneys from patients with diabetic nephropathy. *Kidney Int.* 57:968-972, 2000.
104. Uchida et al., Protein modification by lipid peroxidation products: formation of malondialdehyde-derived N(epsilon)-(2-propenol)lysine in proteins. *Arch. Biochem. Biophys.* 346:45-52, 1997.
105. Ukeda et al., Spectrophotometric assay of superoxide anion formed in Maillard reaction based on highly water-soluble tetrazolium salt. *Anal. Sci.* 18:1151-1154, 2002.
106. Ulrich and Cerami, Protein glycation, diabetes & aging. *Recent Prog. Horm. Res.* 56:1-21, 2001.
107. United Kingdom Prospective Diabetes Study (UKPDS: 10) (1993) Urinary albumin excretion over 3 years in diet-treated Type 2, (non-insulin dependent) diabetic patients, and association with hypertension, hyperglycemia and hypertriglyceridaemia. *Diabetologia* 36:1021-1029, 2003.
108. United Kingdom Prospective Diabetes Study Group (1998). Intensive blood-glucose control with sulphonylureas or insulin compared with conventional treatment and risk of complications in patients with type 2 diabetes (UKPDS 33). *Lancet* 352:837-853, 1998.
109. van Leiden et al., Blood pressure, lipids, and obesity are associated with retinopathy: the Hoorn Study. *Diabetes Care* 25: 1320-1325, 2002.
110. Vlassara et al., Advanced glycation end-products induce glomerular sclerosis and albuminuria in normal rats. *Proc. Natl. Acad. Sci. USA* 91:11704-11708, 1994.
111. Vlassara, The AGE-receptor in the pathogenesis of diabetic complications. *Diabetes Metab. Res. Rev.* 17:436-443, 2001.
112. Vlassara and Palace, Diabetes and advanced glycation endproducts. *J. Intern. Med.* 251:87-101, 2002.
113. Voziyan et al., A post-Amadori inhibitor pyridoxamine also inhibits chemical modification of proteins by scavenging carbonyl intermediates of carbohydrate and lipid degradation. *J. Biol. Chem.* 277:3397-3403, 2002.
114. Voziyan et al., Modification of proteins In vitro by physiological levels of glucose: Pyridoxamine inhibits conversion of amadori intermediate to advanced glycation endproducts through binding of redox metal ions. *J. Biol. Chem.* 2003 Sep. 15 [Epub ahead of print].
115. Wautier et al., Activation of NADPH oxidase by AGE links oxidant stress to altered gene expression via RAGE. *Am. J. Physiol. Endocrinol. Metab.* 280:E685-E694, 2001.
116. Wendt et al., RAGE drives the development of glomerulosclerosis and implicates podocyte activation in the pathogenesis of diabetic nephropathy. *Am. J. Pathol.* 162:1123-1137, 2003.
117. Wilkinson-Berka et al., ALT-946 and aminoguanidine, inhibitors of advanced glycation, improve severe nephropathy in the diabetic transgenic (mREN-2) 27 rat. *Diabetes* 51:3283-3289, 2002.
118. Wolff, Diabetes mellitus and free radicals. Free radicals, transistion metals and oxidative stress in the aetiology of diabetes mellitus and complications. *Br. Med. Bull.* 49:642-652, 1993.
119. Yan et al., Glycation, inflammation, and RAGE: a scaffold for the macrovascular complications of diabetes and beyond. *Circ. Res.* 93:1159-1169.
120. Yang et al., AGE-breakers cleave model compounds, but do not break Maillard crosslinks in skin and tail collagen from diabetic rats. *Arch. Biochem. Biophys.* 412:42-46, 2003.
121. Yim et al., Free radicals generated during the glycation reaction of amino acids by methylglyoxal. A model study of protein-cross-linked free radicals. *J. Biol. Chem.* 270: 28228-28233, 1995.
122. Zheng et al., Prevention of diabetic nephropathy in mice by a diet low in glycoxidation products. *Diabetes Metab. Res. Rev.* 18:224-237, 2002.

EXAMPLES

Example 1

Treatment of Diabetic and Control Rats

Male Sprague-Dawley rats (about 175 to 200 g) were adapted for one week prior to treatment, then rendered diabetic by intra-peritoneal injection of STZ (65 mg/kg in citrate buffer, pH 4.5) after an overnight fast. Control (non-diabetic) animals were injected with the buffer only. Diabetes was confirmed by measuring the plasma glucose concentrations 7 days after Streptozotocin (STZ)-injection. Only animals with a plasma glucose concentration greater than 20 mmol were classified as diabetic and used in the study. These diabetic rats were divided randomly into an untreated diabetic control group and a diabetic treatment group. The treatment group received an LR compound at 50 mg/l in their drinking water throughout the duration of the study (32 weeks for LR-90; 30 weeks for LR-9 and LR-74). All animals were housed individually and were given free access to food and water.

Blood (from the tail vein) and urine samples were collected from rats for glycemic control analysis and albuminuria measurements. Glycemia was monitored every 8 weeks by measuring plasma glucose and glycated hemoglobin. Plasma or serum also was tested for total cholesterol and total triglycerides. Progression of renal dysfunction was assessed by measuring urinary albumin to creatinine ratio (UA/Cr) and serum or plasma creatinine. For measurement of urinary albumin and creatinine concentrations, rats were housed in metabolic cages for 24 hours and urine was collected in a collection beaker with several drops of toluene to inhibit microbial growth.

At the end of study, the rats were weighed and anaesthetized with isoflourane and blood was drawn by heart puncture and transferred into heparinized and non-heparinized vacutainer tubes on ice. These blood samples were later centifuged for plasma and serum collection respectively, and stored at −70° C. until the time of analysis. Rats were killed by over-anesthetization and cardiac puncture and the kidneys were removed immediately, weighed, decapsulated and rinsed in PBS buffer. Sections of the kidneys were stored in 10% NBF for subsequent microscopic examinations and immunohistochemistry. The tail of each individual rat was cut, removed and stored in 50 mL conical tubes at −70° C.

Diabetic rats had significantly increased plasma glucose and glycated hemoglobin concentrations compared with control rats ($p<0.01$). See Tables I and II. Diabetes was also associated with reduced weight gain. Treatment of diabetic rats with compounds LR-9, LR-74 and LR-90 did not affect plasma glucose and glycated hemoglobin, but did result in a moderate increase in weight compared to the diabetic control rats (with only the LR-90 treatment showing statistical significance). Several diabetic rats treated with the LR compounds did not reach the end of the study period, but the incidence was not increased compared with the diabetic controls. Additionally, no mortality was recorded from non-diabetic control rats and those non-diabetic rats treated with all the LR compounds.

Statistical analyses of data presented in this example and the following examples were first analyzed by ANOVA and post-hoc comparisons between group means were analyzed using unpaired Student's t test. A p value of less than 0.05 was considered statistically significant. Data are presented as means±SD.

TABLE I

Effects of LR-90 on Body Weight and Glycemia in STZ-Diabetic Rats (32 Week Treatment).

| Group | n | Body Weight (g) | Plasma Glucose (mmol/l) | HbA1c (%) |
|---|---|---|---|---|
| ND[a] | 4 | 691.0 ± 94.1 | 7.5 ± 1.0 | 1.4 ± 0.1 |
| ND + LR-90 | 4 | 723.0 ± 21.9 | 6.8 ± 0.7 | 1.5 ± 0.1 |
| D[a] | 5 | 267.2 ± 71.3 | 31.3 ± 5.3[b] | 3.8 ± 0.2[b] |
| D + LR-90 | 6 | 337.6 ± 26.6[c] | 28.9 ± 3.4 | 3.3 ± 0.4 |

[a]ND = non-diabetic; D = diabetic
[b]$p < 0.05$ vs. non-diabetic control rats
[c]$p < 0.05$ vs. diabetic rats

TABLE II

Effects of LR-9 and LR-74 on Body Weight and Glycemia in STZ-Diabetic Rats (30 Week Treatment).

| Group | n | Body Weight (g) | Plasma Glucose (mmol/l) | HbA1c (%) |
|---|---|---|---|---|
| ND[a] | 4 | 668.5 ± 65.5 | 8.5 ± 0.7 | 0.90 ± 0.08 |
| ND + LR-9 | 4 | 681.0 ± 9.3 | 8.2 ± 0.9 | 0.90 ± 0.08 |
| ND + LR-74 | 4 | 744.0 ± 51.8 | 6.8 ± 0.8 | 0.87 ± 0.12 |
| D[a] | 5 | 250.8 ± 43.3[b] | 26.5 ± 2.3[b] | 2.06 ± 0.09 |
| D + LR-9 | 6 | 288.0 ± 71.8 | 27.1 ± 1.3 | 1.95 ± 0.22[b] |
| D + LR-74 | 6 | 314.7 ± 53.0 | 26.9 ± 1.5 | 2.10 ± 0.30 |

[a]ND = non-diabetic; D = diabetic
[b]$p < 0.05$ vs. non-diabetic control rats
[c]$p < 0.05$ vs. diabetic rats Example 2

Effects on Lipid Metabolism

Figure 3A:
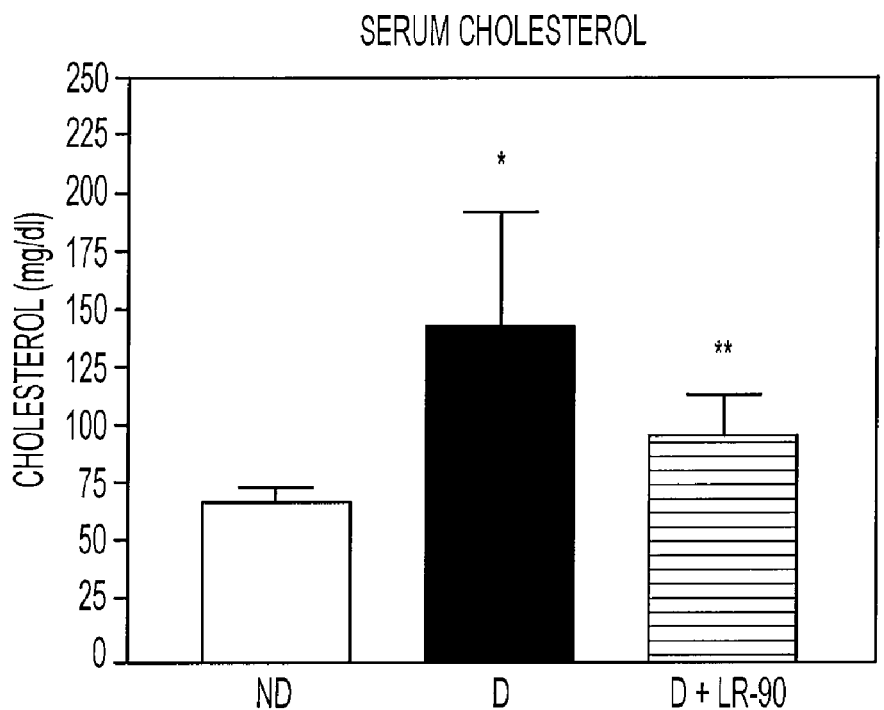
FIG. 3 shows total serum triglycerides (3B) and cholesterol (3A), measured in non-diabetic animals (ND), diabetic animals (D) and diabetic animals treated with LR-90 for 32 weeks (* indicates $p<0.05$ vs. non-diabetic control; **=$p<0.05$ vs. diabetic control).
Figure 3B:
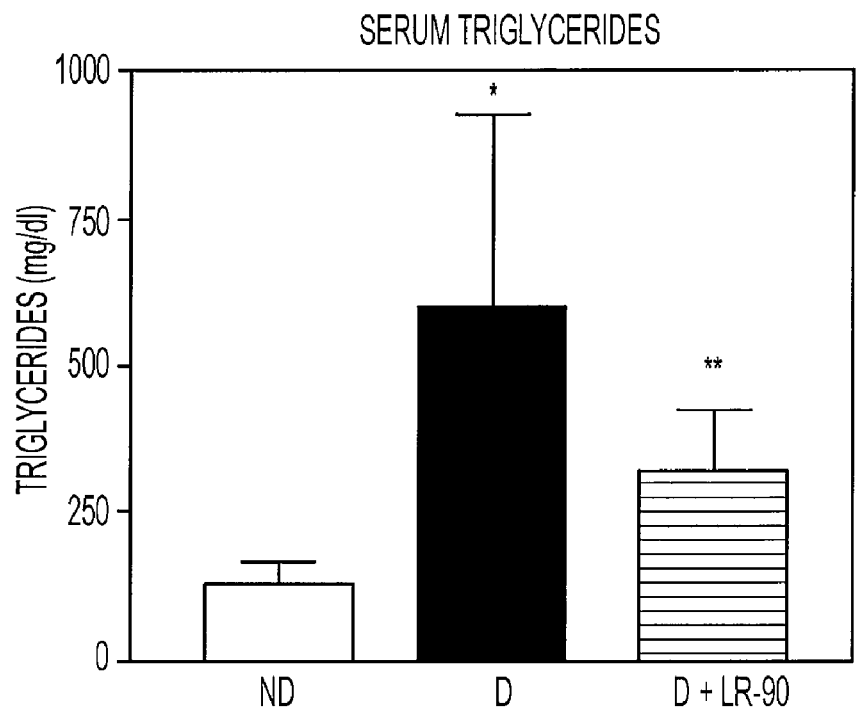
Figure 4A:
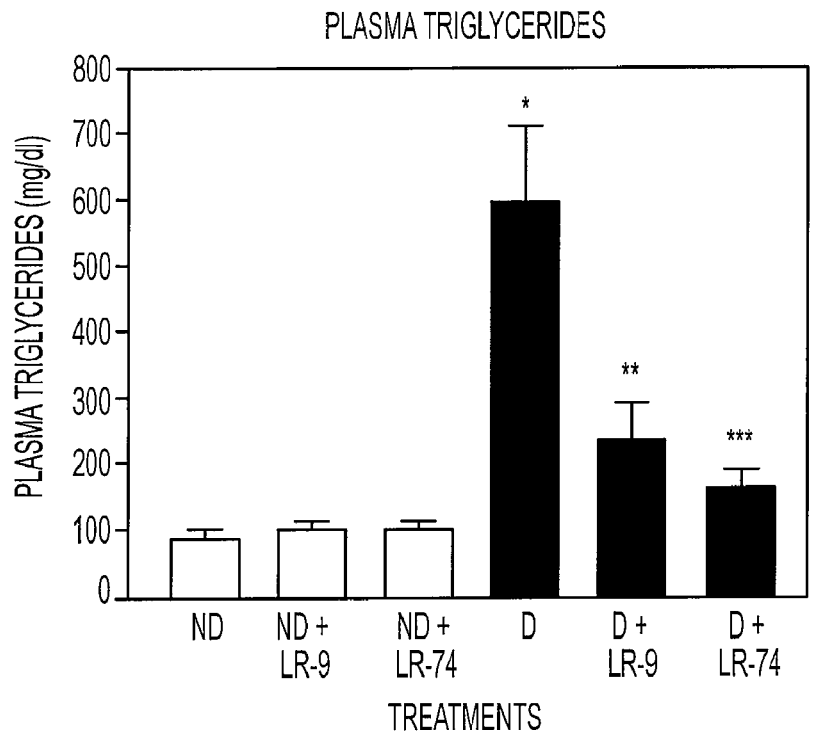
FIG. 4 shows total plasma triglycerides (4A) and cholesterol (4B), measured in non-diabetic animals (ND), diabetic animals (D) and diabetic animals treated with LR-9 or LR-74 for 30 weeks (* indicates $p<0.05$ vs. non-diabetic control; **=$p<0.05$ vs. diabetic control).
Figure 4B:
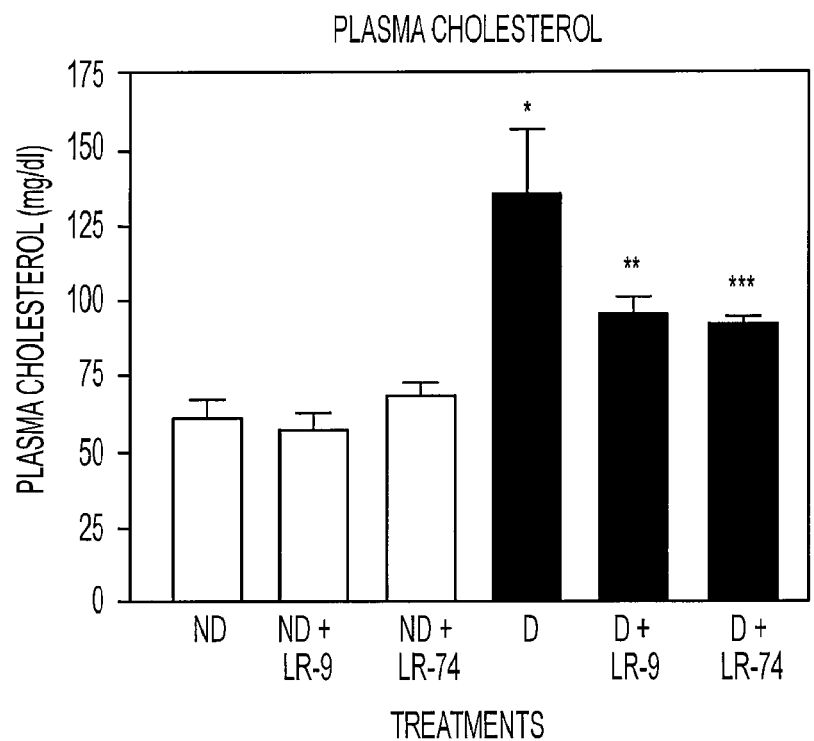

Diabetic rats showed elevated levels of both total plasma/serum triglycerides and cholesterol compared with non-diabetic rats ($p<0.001$). See FIG. 3. Diabetic rats treated with any of the LR compounds showed significant reduction in both triglyceride and cholesterol concentrations. LR-90 reduced serum triglycerides and serum cholesterol by 50% towards levels of non-diabetic animals (FIG. 3). Similarly, plasma triglycerides and cholesterol levels of diabetic rats were also reduced by more than 60% and 50%, respectively by both LR-9 and LR-74 (FIG. 4).

Example 3

Effects on Renal Function

Urinary albumin, plasma creatinine concentration, and urinary albumin/creatine ratio (UA/Cr) were used as indicators of renal function. Compared with non-diabetic control rats, urinary albumin excretion, plasma creatine concentration and UA/Cr increased significantly in diabetic animals. #See Tables III and IV. Treatment of diabetic rats with the LR compounds inhibited the rise in urinary albumin excretion and UA/Cr, with about a 50% reduction in concentration compared to untreated diabetics rats. In addition, the elevated plasma creatinine concentrations observed in diabetic animals were significantly decreased by almost 50% with treatment of either LR-9, LR-74 or LR-90.

TABLE III

Effects of LR-90 on Renal Function Parameters in STZ-diabetic Rats.

| Group | Plasma Creatine (mg/dl) | Urinary Albumin (mg/24 hr) | Urinary Albumin/Creatine Ratio |
|---|---|---|---|
| ND[a] | 0.46 ± 0.07 | 7.6 ± 0.8 | 0.49 ± 0.24 |
| ND + LR-90 | 0.58 ± 0.07 | 8.9 ± 1.5 | 0.57 ± 0.16 |
| D[a] | 2.94 ± 0.90[b] | 37.5 ± 8.4[b] | 3.32 ± 1.37[b] |
| D + LR-90 | 1.50 ± 0.53[c] | 23.6 ± 4.5[c] | 1.57 ± 0.49[c] |

[a]ND = non-diabetic; D = diabetic
[b]$p < 0.05$ vs. non-diabetic control rats
[c]$p < 0.05$ vs. diabetic rats

TABLE IV

Effects of LR-9 and LR-74 on Renal Function Parameters in STZ-diabetic Rats.

| Group | Plasma Creatine (mg/dl) | Urinary Albumin (mg/24 hr) | Urinary Albumin/Creatine Ratio |
|---|---|---|---|
| ND[a] | 0.45 ± 0.11 | 4.8 ± 1.8 | 0.34 ± 0.10 |
| ND + LR-9 | 0.42 ± 0.02 | 4.8 ± 2.3 | 0.33 ± 0.13 |
| ND + LR-74 | 0.42 ± 0.05 | 4.6 ± 2.4 | 0.30 ± 0.16 |
| D[a] | 3.13 ± 0.85[b] | 32.8 ± 8.0[b] | 2.91 ± 0.85[b] |
| D + LR-9 | 1.79 ± 0.95[c] | 18.0 ± 9.1[c] | 1.36 ± 0.93[c] |
| D + LR-74 | 1.64 ± 1.07[c] | 14.3 ± 9.07[c] | 1.23 ± 0.60[c] |

[a]ND = non-diabetic; D = diabetic
[b]$p < 0.05$ vs. non-diabetic control rats
[c]$p < 0.05$ vs. diabetic rats Example 4

Effects on Serum AGE

Serum AGE was measured according to the methods of Al-Abed et al., *Meth. Enzymol* 309:152-172, 1999 and quantitated with polyclonal R6/9 anti-AGE RNAse antibodies using the methods of Rahbar et al., *Biochem. Biophys. Res. Commun.* 262:651-656, 1999. One AU was assumed equivalent to 1 µg/ml AGE-BSA.

Figure 5:
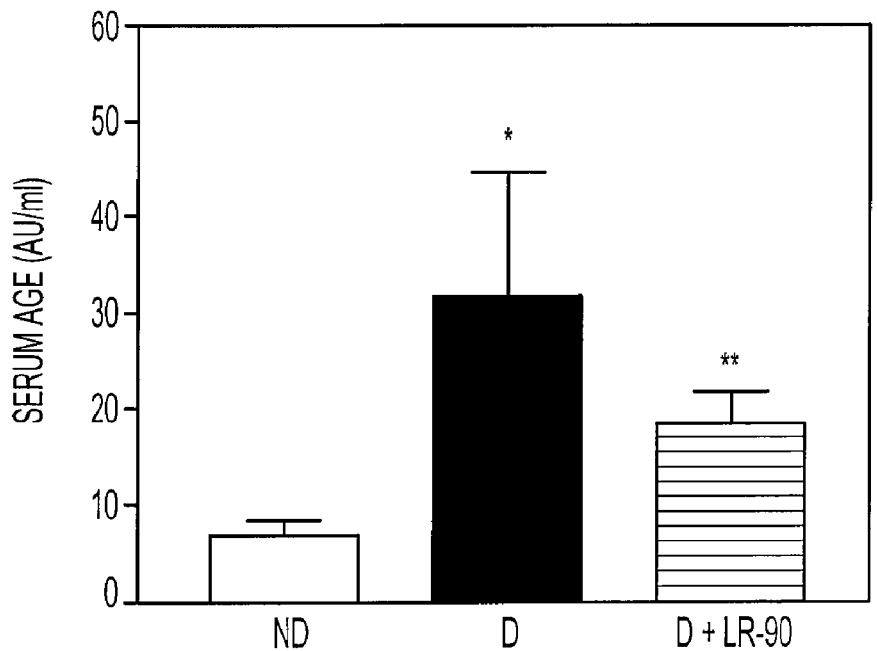
FIG. 5 shows the effect of LR compounds on serum AGE after LR-90 treatment for 32 weeks. Serum AGE concentration was measured immunologically using anti-AGE RNAse polyclonal antibodies. *=$p<0.05$ vs. non-diabetic control; ** $p<0.05$ vs. diabetic control.
Figure 6:
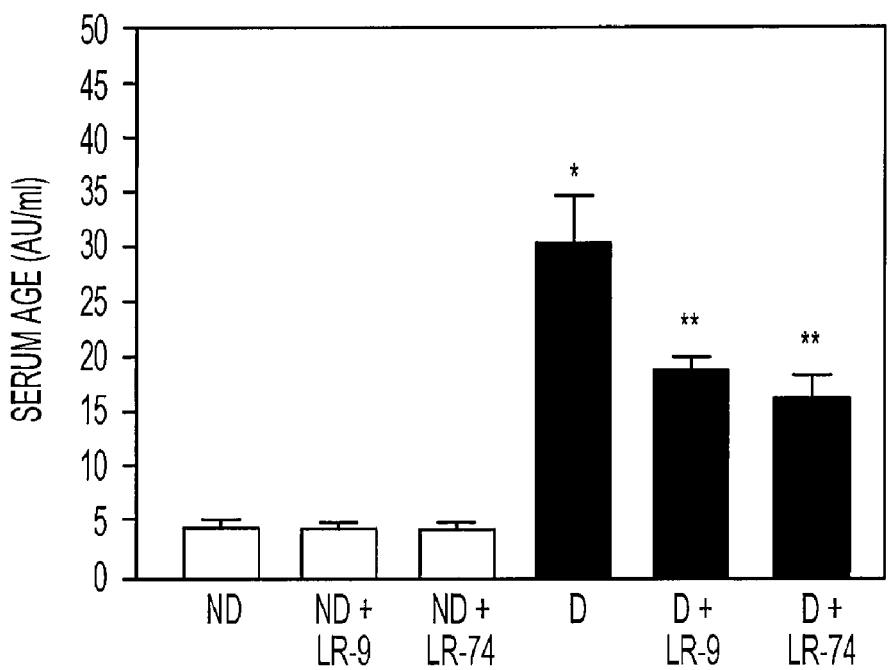
FIG. 6 shows the effect of LR compounds on serum AGE after LR-9 or LR-74 treatment for 30 weeks. Serum AGE concentration was measured immunologically using anti-AGE RNAse polyclonal antibodies. *=$p<0.05$ vs. non-diabetic control; ** $p<0.05$ vs. diabetic control.

Diabetic rats had about five-fold increase in levels of serum AGE compared to non-diabetic rats (p<0.05). See FIGS. 5 and 6. Diabetic rats treated with the LR compounds markedly reduced the AGE concentration by as much as 50%.

Example 5

Collagen Crosslinking, Fluorescence, and Acid Solubility

Isolation and preparation of tail tendon collagen was performed according to Kochakian et al., *Diabetes* 45:1694-1700, 1996. The relative degree of crosslinking and AGE formation in collagen was assessed by pepsin digestion and acid solubility. Pepsin digestion was performed as described previously by Stefek et al., *Biochim. Biophys. Acta* 1502:398-404, 2000. Briefly, collagen samples of 10 mg from individual rats were digested with pepsin (50 µg/mL in 0.5 mol/l acetic acid) for 24 hours at 37° C. After digestion, the samples were centrifuged at 3000 rpm for 30 minutes at 4° C. and the clear supernatant containing the digested collagen was collected. One hundred microliter aliquots of the supernatant were mixed with 900 µL PBS buffer for measurement of the fluorescence of the sample at 365 nm excitation and 418 nm emission. The hydroxyproline content of the supernatant was calculated following acid hydrolysis using a microassay method according to known methods (Creemers et al., *Biotechniques* 22:656-658, 1997).

The acid solubility of tail tendon collagen was measured by a modification of the method outlined in Yang et al., *Arch. Biochem. Biophys.* 412:42-46, 2003. Briefly, samples of about 2 mg collagen were weighed and solubilized in 0.05 M acetic acid overnight at 4° C. The suspensions were centrifuged at 20,000 g 60 minutes at 4° C. and the supernatants and pellets were separated for analysis of hydroxyproline content following acid hydrolysis. Acid solubility was calculated as the percentage of hydroxyproline in the supernatant divided by the total hydroxyproline content in the pellet and the supernatant.

Figure 7A:
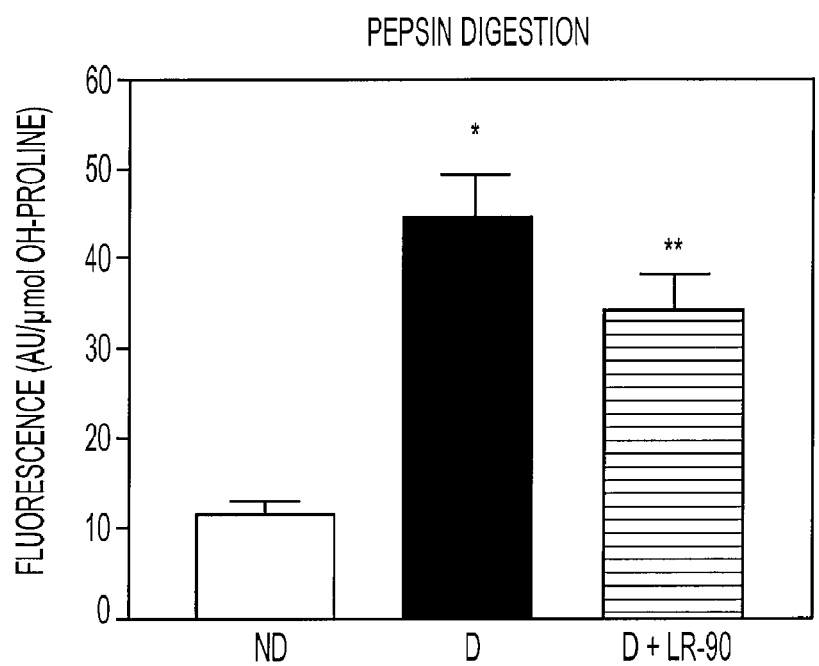
(FIG. 7A: LR-90.
Figure 7B:
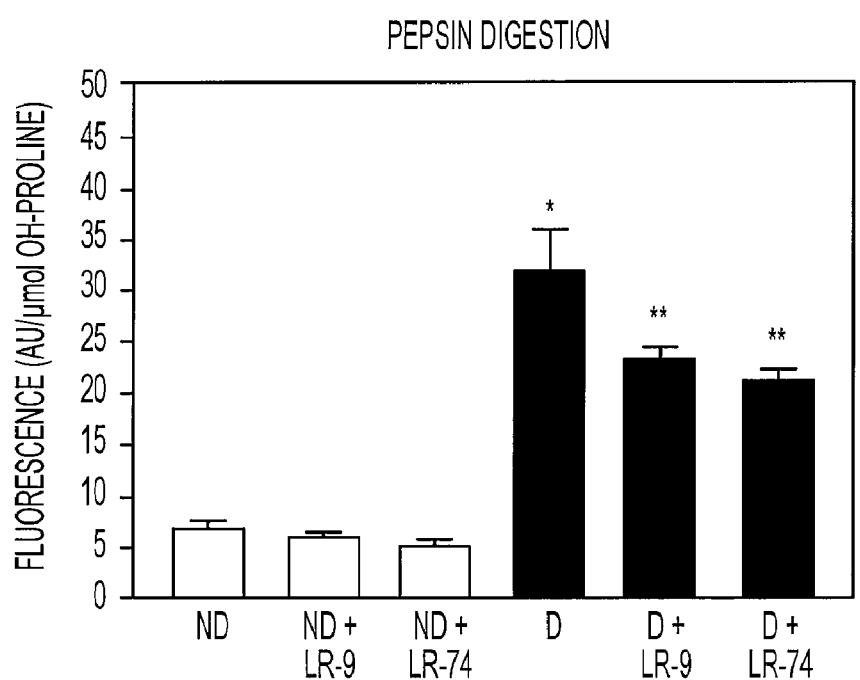
FIG. 7B: LR-9 and LR-74). * indicates $p<0.05$ vs. non-diabetic control; ** indicates $p<0.05$ vs. diabetic control.
Figure 8:
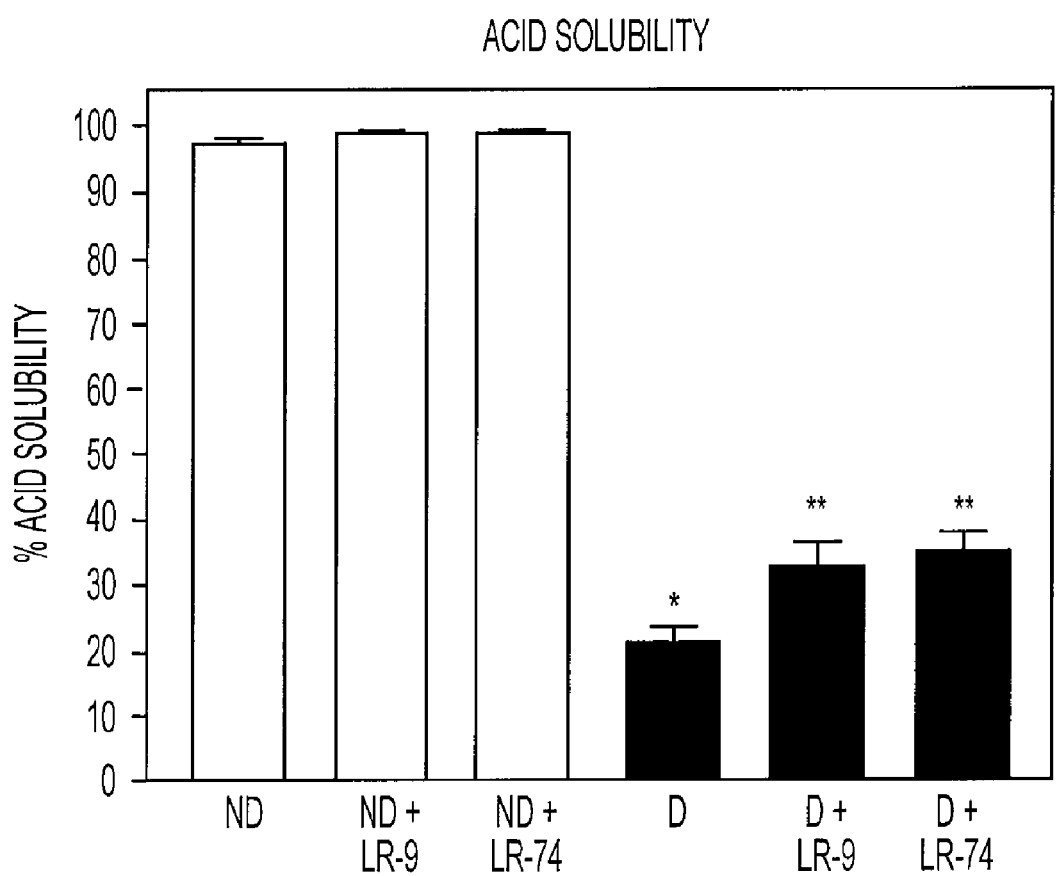
FIG. 8 shows the effect of LR compounds on rat tail tendon crosslinking measured by solubility in weak acid. * indicates $p<0.05$ vs. non-diabetic control; ** indicates $p<0.05$ vs. diabetic control.

Levels of fluorescent AGE in tail collagen were increased about fourfold in diabetic rats compared to non-diabetic animals. LR-treated diabetic rats showed a significant reduction of fluorescence and crosslinking compared with the untreated diabetic animals (FIG. 7A: LR-90; FIG. 7B: LR-9 and LR-74). Similarly, when tail tendon collagen was solubilized in weak acetic acid, the collagen of diabetic rats showed very low solubility in the acid solution. Diabetic rats that received the LR compounds significantly increase the acid solubility of the tail tendon collagen (FIG. 8).

Example 6

LR Compound Effects on Kidney Anatomy and Histopathology

To quantitate glomerulosclerosis (defined as glomerular basement membrane thickening, mesangial hypertrophy, and capillary occlusion), kidney sections were stained with periodic acid Schiff (PAS) reagent. A total of 150 glomeruli were randomly chosen from each rat kidney (four different kidneys per treatment) and carefully graded for sclerosis, by a blinded evaluator. The degree of sclerosis in each glomerulus was graded subjectively on a scale of 1 to 4 as follows: grade 1, sclerotic area less than 25%; grade 2, sclerotic area 25-50%; grade 3, sclerotic area 51-75%; and grade 4, sclerotic area more than 75%. The glomerulosclerotic index (GSI) then was calculated using the following formula: $GSI = \Sigma_{i=1}^{4} Fi\ (I)$, where Fi is the percentage of glomeruli in the rat with a given score of (I). See Wilkinson-Berka et al., *Diabetes* 51:3283-3289, 2002. To quantitate glomerulosclerosis, kidney sections were stained with periodic acid Schiff (PAS) reagent.

Cellular infiltrates were identified in the renal interstitium from 5 µm-thick kidney sections stained with PAS. Infiltrates in each kidney sample were graded as follows: + (patchy and light), ++ (patchy and dense), +++ (diffuse and dense with aggregates of neutrophils in tubules or in interstitium) also in a blinded manner. For collagen deposition staining in the kidneys, paraffin sections were randomly chosen from kidneys from each treatment group and stained with Masson's trichrome. Briefly, the sections were deparaffined, hydrated with water, and immersed in Mordant in Boiuin's solution for 10 minutes. The sections then were rinsed in water and stained with Mayer's hematoxylin for 6 minutes. After rinsing in water, Biebrich scarlet-acid fuchsin was added for 2 minutes, rinsed, phosphomolybdic-phosphotungstic solution added for 15 minutes, followed by aniline blue solution for 10 minutes. After rinsing the sections with water, glacial acetic acid was added for 20 seconds and then the slides were dehydrated with 95% ethanol. With this method, blue and red colors indicate collagen and cytoplasm staining, respectively. Degenerated tubules were identified by the absence of cytoplasm. Additional staining for collagen fiber deposition in the glomeruli was performed using Picrosirius red staining.

For examination of renal morphometry, kidney samples from each group were post-fixed with 2% glutaraldehyde overnight in cacodylate buffer. Sections were cut to 1 µm thickness and stained with Toluidine Blue. Then 80 nm sections were cut with a diamond knife, picked up on formvar-coated, carbon-coated slot copper grids and stained with 5% aqueous uranyl acetate for 15 minutes, followed by 2 minutes' incubation on a drop of lead citrate. The grids were observed and photographed with a high resolution transmission electron microscope. The images were used to determine the width of the glomerular basement membrane and mesangial expansion.

Mean kidney weights, both in absolute weight and as a fraction of total body weight, were significantly increased in diabetic rats compared to non-diabetic animals, but there were no statistically significant differences detected between kidney weight of LR-treated and untreated diabetic control rats. Occasional cysts were observed in kidneys of diabetic control animals, but these were not more frequent in LR-treated rats. Moreover, there was no evidence of tumor growths in other major organs (heart, liver, intestines) from both untreated and LR-treated diabetic animals.

Figure 9:
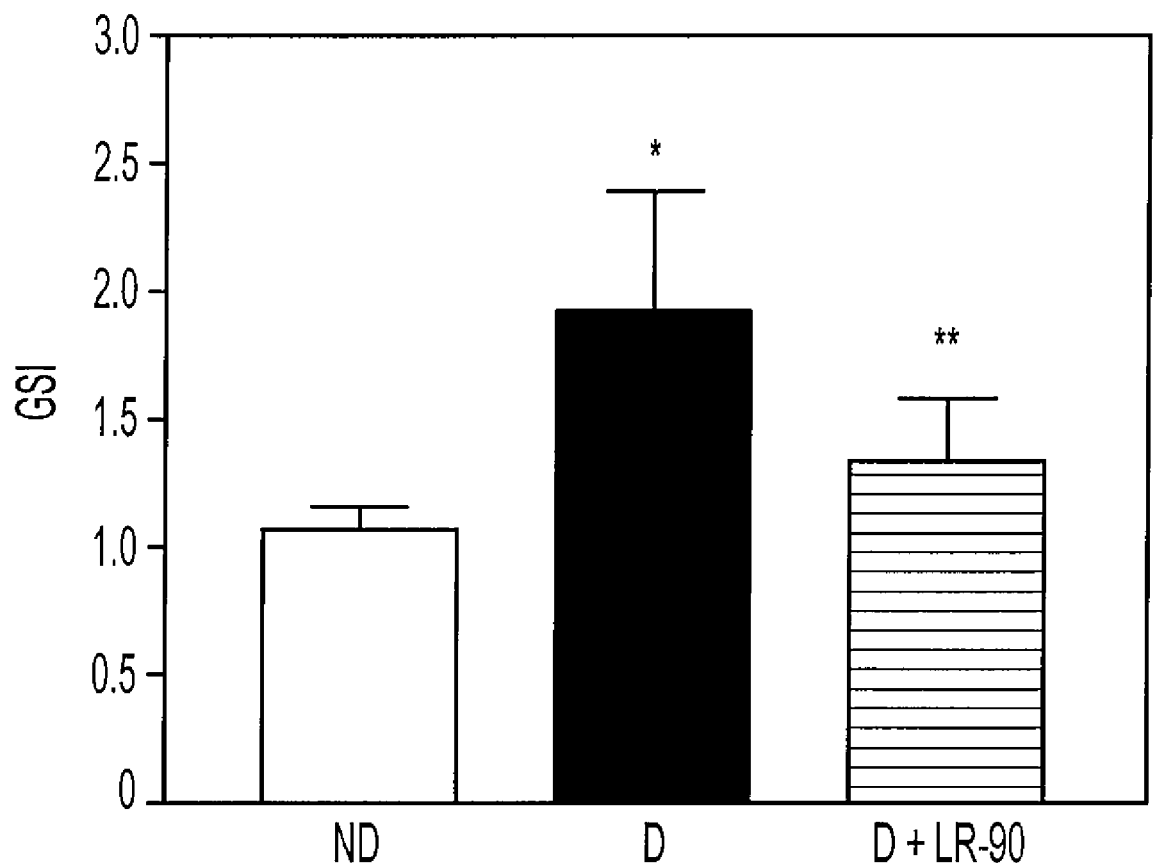
FIG. 9 Shows the effect of LR-90 on the degree of glomerulosclerosis in diabetic rats. Glomerulosclerotic index (GSI) was calculated from 150 glomeruli in each rat. * indicates $p<0.05$ vs. non-diabetic control; ** indicates $p<0.05$ vs. diabetic control.
Figure 10A:
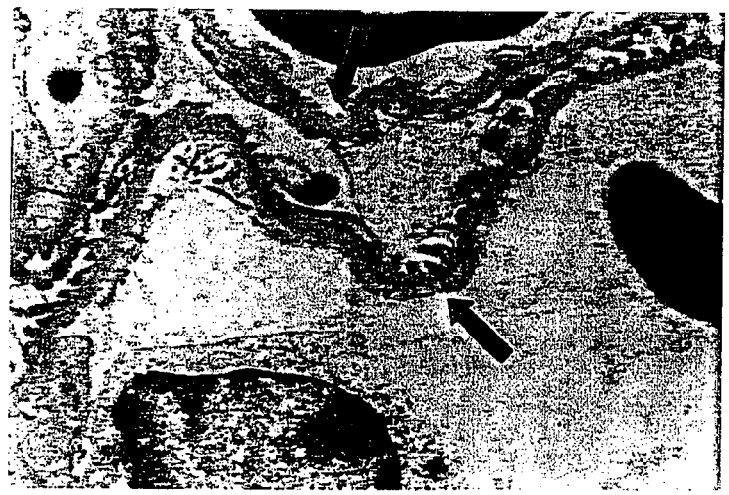
FIG. 10 is a series of photographs showing LR-90 reduced basement membrane thickening. Kidney sections were cut and photographed using high resolution TEM to show basement membrane expansion and thickening.
Figure 10B:
Figure 10C:

No considerable ultrastructural abnormalities in kidneys were detected from the non-diabetic rats, except for few thickened basement membranes and a few cases of glomerulosclerosis (FIG. 9). Most of the glomeruli showed a normal ultrastructural appearance with normal cellularity, a normal mesangium, and a basement membrane of about 150 nm as revealed by TEM (FIG. 10). No cellular infiltrates were detected in the renal interstitium from these animals. In untreated diabetic rats, TEM data indicated that many glomeruli showed thickened basement membranes (about 270 nm) with markedly increased cellularity and increased mesangial cells and matrix (FIG. 10), and this was reflected by an increased GSI (FIG. 9). Also, there were a number of cellular infiltrates observed, including dense aggregates of lymphocytes and neutrophils (data not shown).

Figure 11A:
(FIG. 11A) non-diabetic.
Figure 11B:
(FIG. 11B), diabetic.
Figure 11C:
(FIG. 11C) diabetic+LR-90.
Figure 12A:
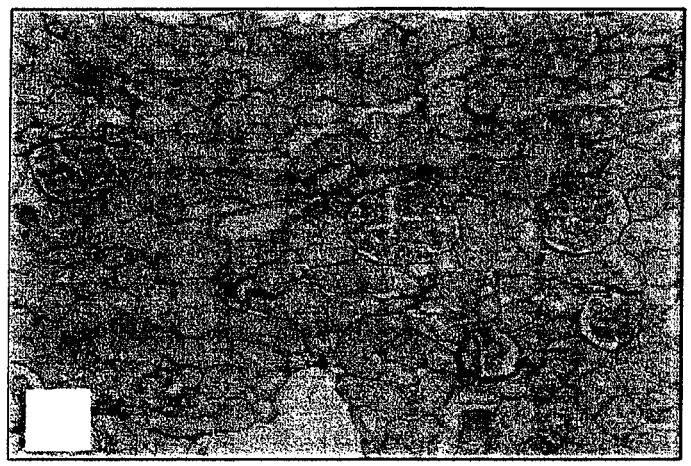
(FIG. 12A) non-diabetic.
Figure 12B:
(FIG. 12B), diabetic.
Figure 12C:
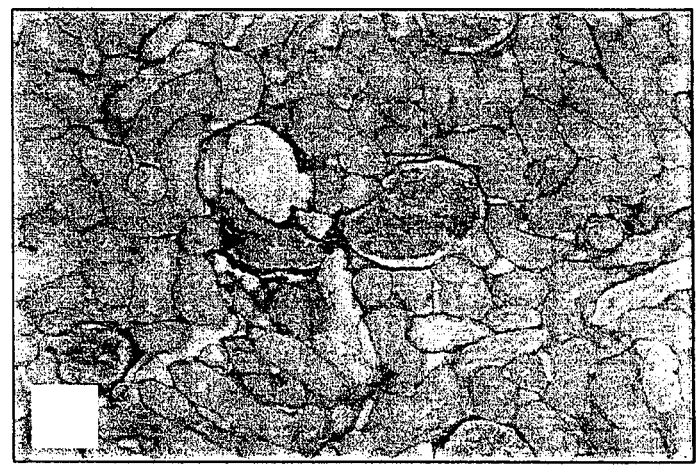
(FIG. 12C) diabetic+LR-90.

Diabetic rats treated with the LR compounds also showed an increase in cellularity, although less markedly than that of untreated diabetic animals. Only lymphocytes were observed in the renal interstitium. In addition, there was less glomerular damage, thinner basement membrane (about 220 nm), and significantly lower GSI than untreated diabetic rats (p<0.05, FIGS. 9 and 10). Moreover, both collagen deposition (blue color) in the tubulointerstitium and glomeruli, and the number of degenerate tubules (identified by the absence of cytoplasm or reddish color), were increased in diabetic rats compared with the non-diabetic controls rats, and LR treatment reduced the amount of collagen staining and frequency of degenerate tubules to an almost similar extent to that of the non-diabetic control rats (FIG. 11). Similar results were observed when the kidneys were stained with Picrosirius red: LR-90 treatment reduced the amount of collagen deposited inside the glomeruli and the tubulointerstitium (FIG. 12).

Example 7

AGE Immunohistochemistry

For immunohistochemical AGE staining, formalin-fixed parafilm embedded sections (2 μm thick) were mounted on slides coated with 2-aminopropyltriethoxy silane, baked for 3 hours at 58° C., deparaffinized, rinsed with 3% hydrogen peroxide, and incubated with Proteinase K (0.5 mg/mL) for 5 minutes at room temperature. These sections were washed with rinse buffer and blocked with Protein Blocking Agent for 5 minutes and subsequently incubated with 6D12 anti-AGE mouse monoclonal antibody specific for CML for 30 minutes at room temperature. After washing with rinse buffer, the sections were incubated with EnVision™ with labeled polymer peroxidase-conjugated mouse anti-IgG for 30 minutes at room temperature, followed by detection with 3,3'-diaminobenzidine tetrahydrochloride solution as chromogen and 50% hematoxylin as counterstain.

Figure 13A:
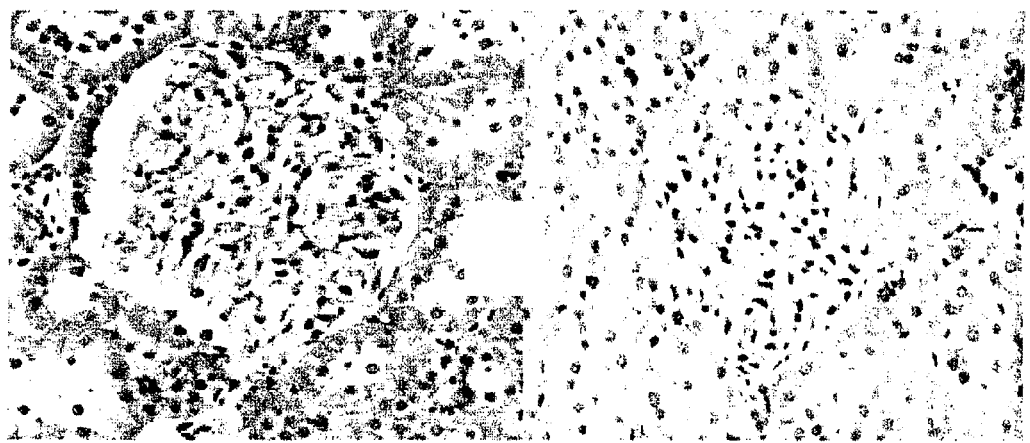
(FIG. 13A) non-diabetic.
Figure 13B:
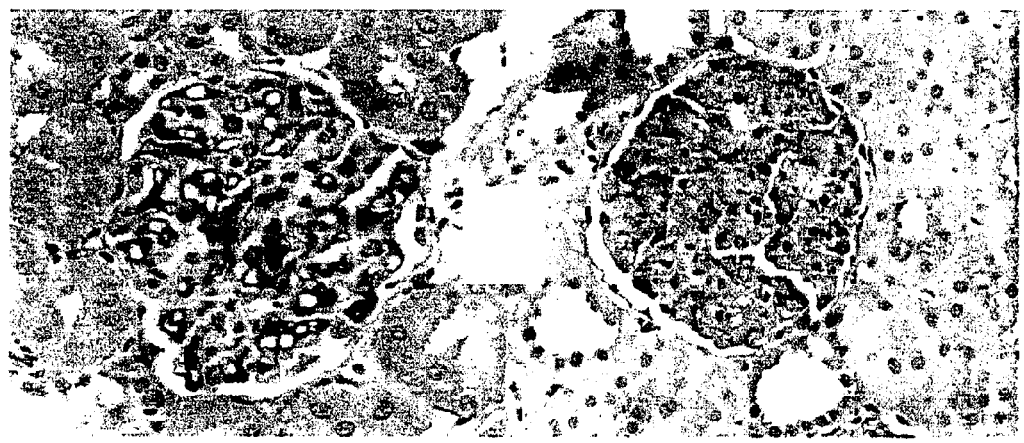
(FIG. 13B), diabetic.
Figure 13C:
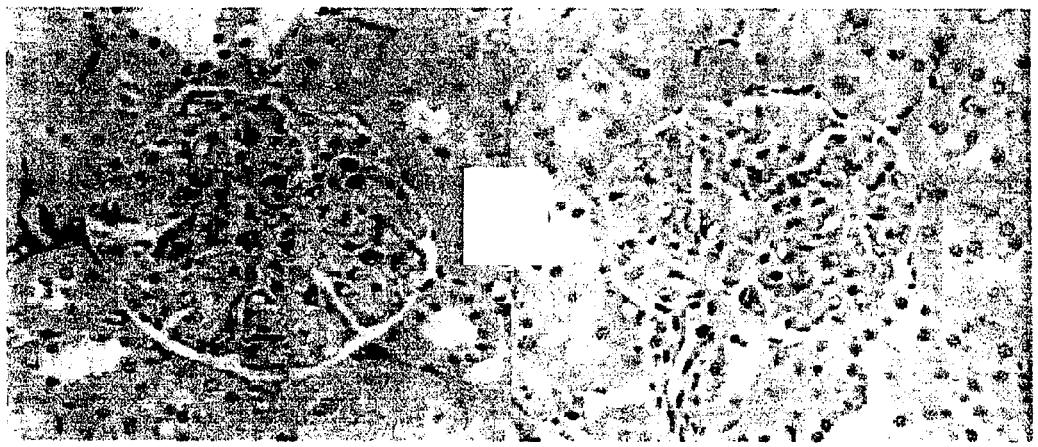
(FIG. 13C) diabetic+LR-90.

Immunohistochemical staining for AGE in rat kidney showed that there was widespread staining for AGE in the kidney glomeruli and the cortical tubules in diabetic rats compared with the non-diabetic control rats. LR-90 treatment visibly reduced the AGE deposited in these regions (FIG. 13). Similar reduction of AGE staining was observed on kidneys of rats treated with LR-9 or LR-74.

Example 8

Nitrotyrosine Staining

Nitrotyrosine, a marker for protein oxidation, was used as an index of oxidative tissue damage caused by reactive nitrogen species. Immunohistochemical detection of nitrotyrosine was performed as reported previously (Forbes et al., *Diabetes* 51:3274-3282, 2002) and followed in this study with little modification. Briefly, formalin-fixed kidney sections (5 μm thick), taken from representative rats from each treatment group at 32 weeks, were mounted on slides, dewaxed and hydrated. After incubation with Proteinase K for 10 minutes, sections were incubated in 3% hydrogen peroxide for 20 minutes, blocked with normal porcine serum for 20 minutes, and then stained with commercially available rabbit polyclonal anti-nitrotyrosine antibodies for 1 hour. After rinsing with DAKO rinse buffer, sections were incubated with biotinylated anti-rabbit IgG for 25 minutes, followed by incubation with avidin-biotin horseradish peroxidase complex for 25 minutes. Localization of peroxidase conjugates was revealed using diaminobenzidine tetrahydrochloride (DAB) solution as chromogen and 50% hematoxylin as counterstain.

Figure 14A:
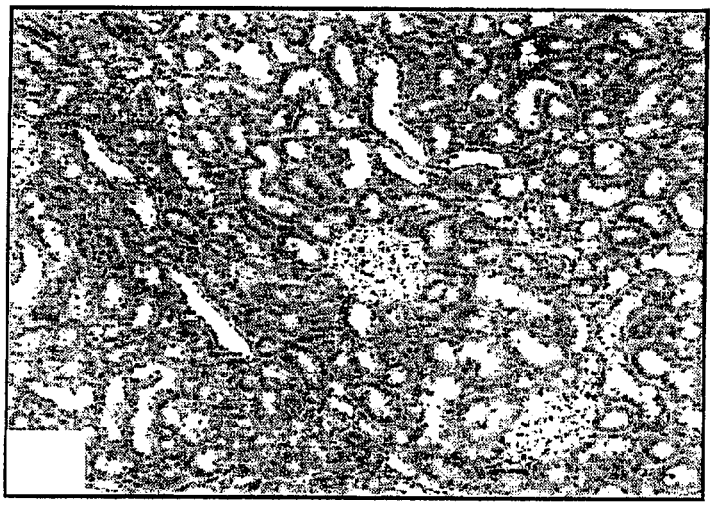
(FIG. 14A) non-diabetic.
Figure 14B:
(FIG. 14B), diabetic.
Figure 14C:
(FIG. 14C) diabetic+LR-90.

Nitrotyrosine was predominantly detected in the renal tubules and little staining was visible in glomeruli. See FIG. 14. Increased nitrotyrosine staining was observed in the renal tubules of diabetic rats compared with non-diabetic animals, and rats treated with either of the LR compounds showed markedly reduced nitrotyrosine staining in the cortical tubules. See FIG. 14.

Example 9

In vitro Tests

In vitro measurement of the kinetics of inhibition of copper-catalyzed oxidation of ascorbic acid was performed according to the methods of Price et al., *J. Biol. Chem.* 276: 48967-48972, 2001. Briefly, $CuCl_2$ and various concentrations of inhibitor compounds were pre-incubated in chelex-treated 20 mmol/L phosphate buffer, pH 7.4, for 5 minutes. Ascorbic acid then was added (50 μL of 10 mmol/L in water) to initiate the reaction (1 mL total reaction volume). The final concentrations of $CuCl_2$ and ascorbic acid in the reaction were 500 nmol/L and 500 μmol/L, respectively. Aliquots (135 μL) were removed at 0 and 60 minutes and transferred to autoinjector vials containing 15 μL of 10 mmol/l DTPA. Samples were analyzed by reversed phase HPLC on an XTerra™ RP18 column (250 mm×4.6 mm, 5 μm) with an XTerra™ RP18 5 μm guard column using a Waters® 2690 Separator Module equipped with auto-injector and Millenium® 32 software. Solvents and gradient were all used as described in Dillon et al., *Life Sci.* 72:1583-1594, 2003. The absorbance of ascorbic acid was measured at 244 nm and the peak area was obtained to estimate the percent of ascorbic acid remaining versus time. For each inhibitor compound, the concentration that inhibited the rate of AA oxidation by 50% ($IC_{50}$), was calculated with respect to the control using Prism™ software.

Figure 15:
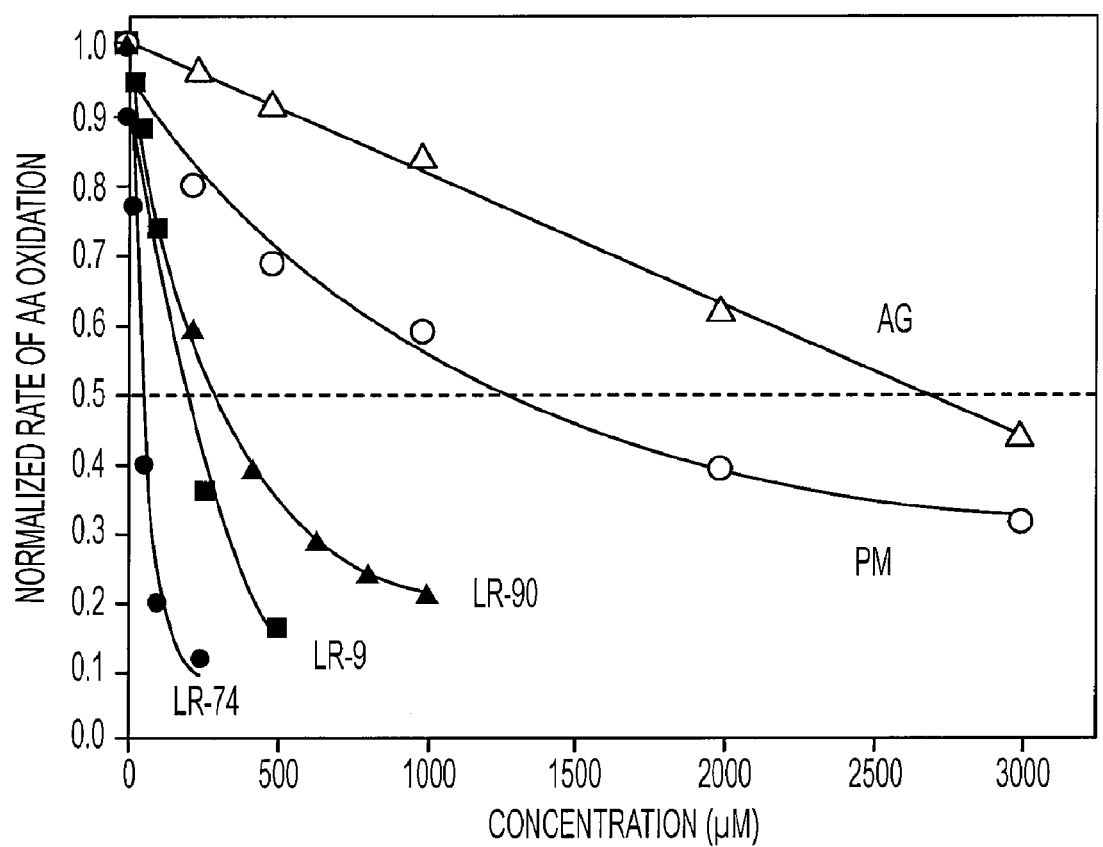
FIG. 15 provides data on inhibition of $Cu^{++}$-catalyzed oxidation of ascorbic acid by LR compounds compared with known AGE inhibitors. The dashed horizontal line indicates 50% loss of AA.

The $Cu^{2+}$, chelating activity of the three LR compounds, aminoguanidine (AG) and pyridoxamine (PM) are shown in FIG. 15. In this assay, the $IC_{50}$ values of LR-9, LR-74, LR-90, PM and AG were 200, 50, 275, 1250 and 2750 μM, respectively. These results indicate that in vitro, LR-74 was the most potent metal chelator among the LR compounds, and all these novel compounds were better metal chelators than both known AGE inhibitors AG and PM.

The ability of the LR compounds to inhibit lipid peroxidation was tested using $Cu^{++}$-mediated lipid oxidation, a common in vitro model for studies on lipoxidative modifications of proteins. The effects of the LR compounds on lipid peroxidation were studied using $Cu^{++}$-mediated oxidation of LDL. Human LDL (50 μg of protein/mL) was incubated at 37° C. in chelex-treated PBS buffer alone or in the presence of 5 μM $CuCl_2$ or 5 μM $CuCl_2$ plus various concentrations of the inhibitor compounds (10-250 μM). After 5 hours of incubation, the amount of thiobarbituric acid reactive substances (expressed as malondialdehyde (MDA) equivalents) generated in the reaction mixture was calculated according to methods described by Dillon et al., *Life Sci.* #72:1583-1594, 2003. Briefly, aliquots from each sample were precipitated with 20% trichloroacetic acid, centrifuged and an equal volume of 1% thiobarbituric acid was added to the supernatant. The samples then were heated to 95° C. for 10 minutes, and upon cooling, the absorbance was read at 532 nm. Hydrolyzed tetraethoxypropane was used as a standard for the MDA equivalent calculation.

Figure 16:
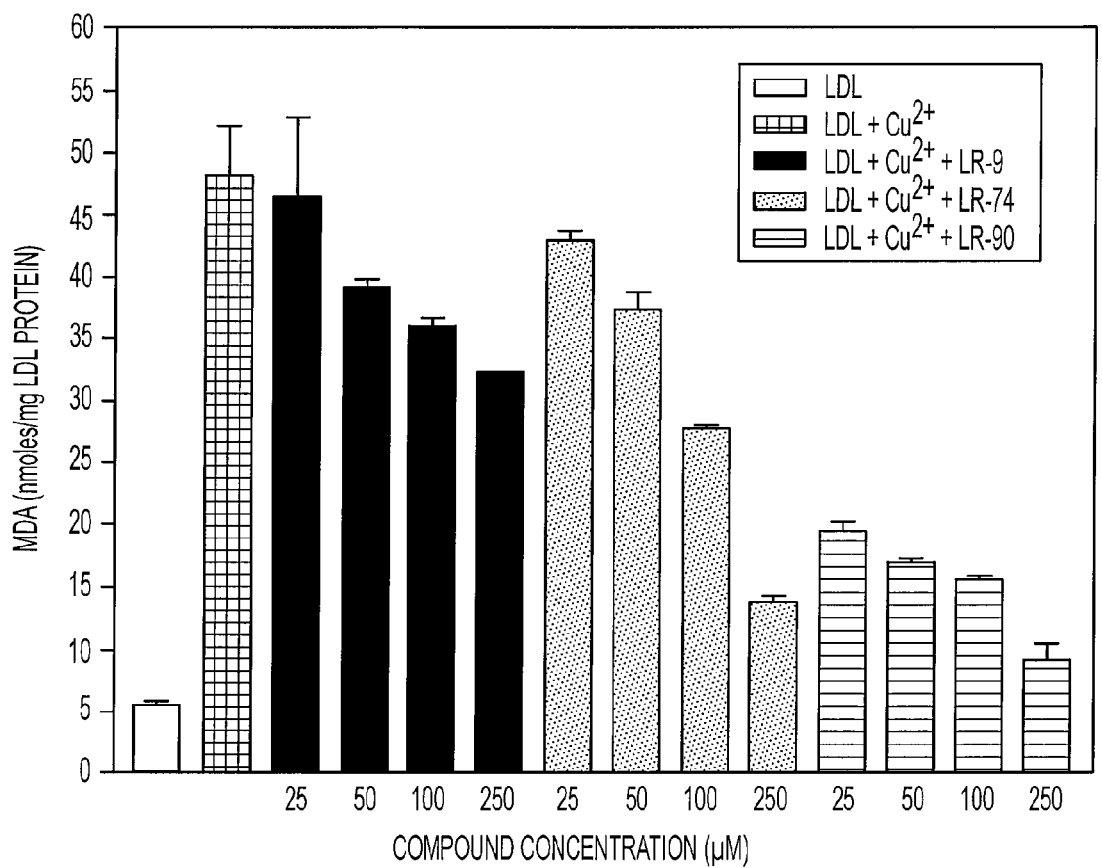
FIG. 16 provides data for inhibition of $Cu^{2+}$-mediated lipid peroxidation by LR compounds.

As shown in FIG. 16, all the LR compounds inhibited LDL oxidation in a concentration-dependent manner. The inhibition activities of LR-74 and LR-90 were better than AG. PM had no effect on lipid peroxidation.

The effects of the compounds on free radical production were evaluated in a cell-free system. In vitro hydroxyl radical production was determined by the hydroxylation of benzoate by $H_2O_2$ as described in Giardino et al., *Diabetes* 47:1114-1120, 1998. In brief, 30 mmol/l sodium benzoate in PBS buffer, pH 7.4, was incubated with 10 mmol/l $H_2O_2$ overnight at 37° C. alone and in the presence of various amounts of inhibitor compounds. After incubation, aliquots from each sample were analyzed for fluorescence (305 nm excitation; 408 nm emission). Results were expressed as the amount of salicylate equivalent (μM) produced by the hydroxylation of benzoate. Mannitol, a known hydroxyl radical scavenger, was included in the experiment as control.

The superoxide radical scavenging activity of the compounds was evaluated using the WST-1 method described in Ukeda et al., *Anal. Sci.* 18:1151-1154, 2002. Briefly, methylglyoxal, was incubated with or without N-α-acetyl-lysine in 0.05 M chelex-treated sodium phosphate buffer, pH 7.4, in the presence of various concentrations of the inhibitor compounds. The production of superoxide was monitored spectrophotometrically at 438 nm, and compared with superoxide dismutase and Tiron, two known superoxide radical scavengers.

Figure 17A:
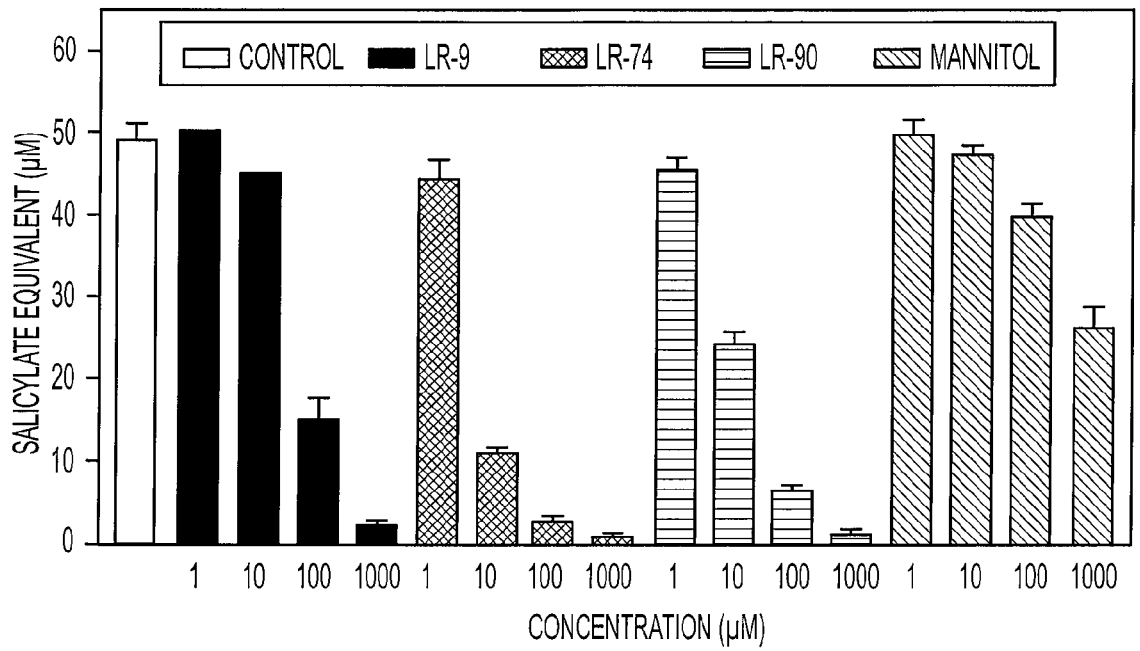
FIG. 17 shows the effect of LR compounds on free radical production. Hydroxyl radicals were measured from the hydroxylation of benzoate by $H_2O_2$ and expressed as salicylate equivalents obtained from salicylic acid standards (17A). Superoxide production was monitored from the reaction with methylgloxal with N-α-acetyl-L-lysine and detected by the WST-1 assay (17B).
Figure 17B:
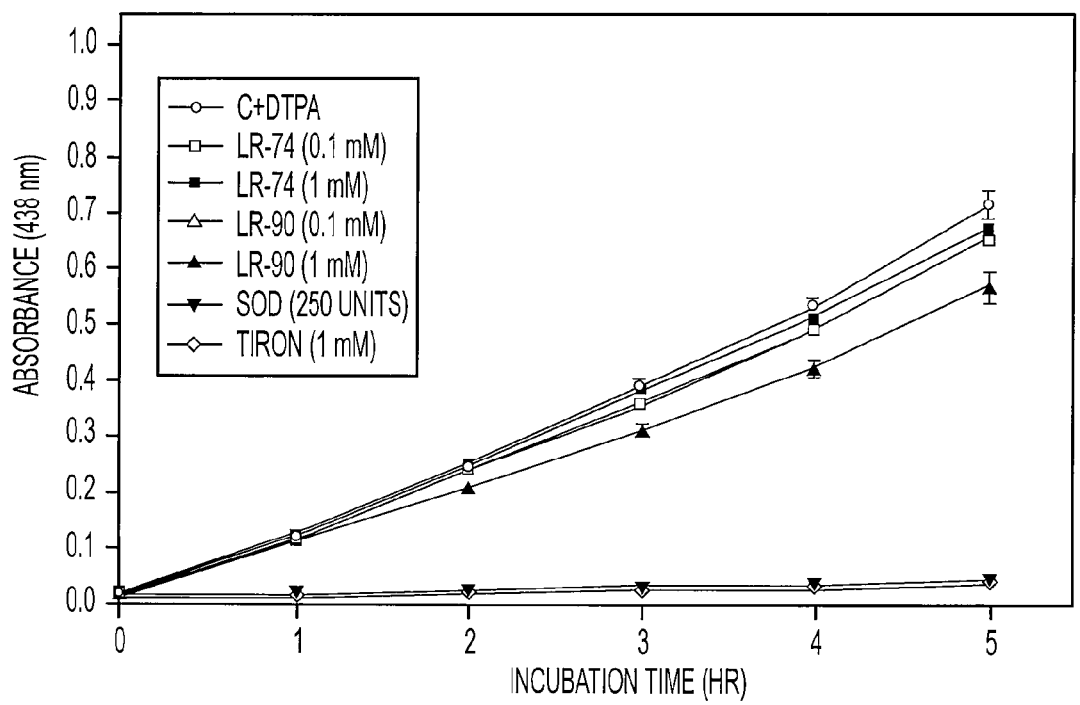
Figure 18A:
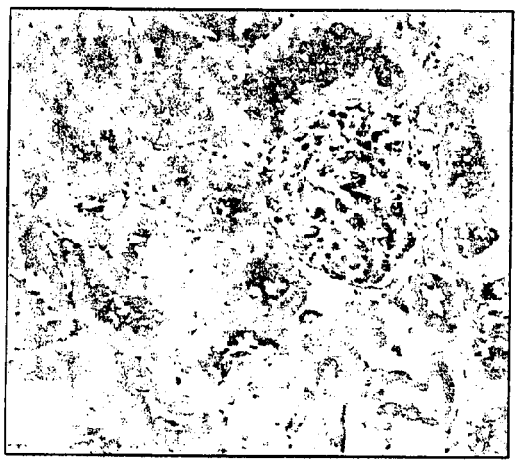
FIG. 18A: ND.
Figure 18B:
FIG. 18B: D.
Figure 18C:
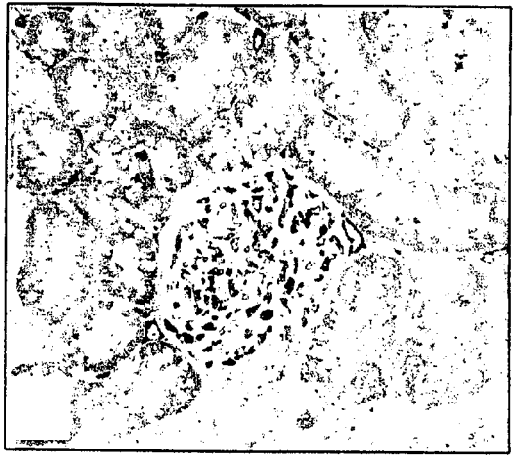
FIG. 18C: D+LR-9.
Figure 18D:
FIG. 18D: D+LR-74.

All three LR compounds inhibited —OH radicals formed from the reaction of hydrogen peroxide with sodium benzoate in a concentration-dependent manner, with greater inhibitory activities than mannitol, a well-known ⁻OH radical scavenger. See FIG. 17A. Using the WST-1 assay to monitor superoxide produced from an actual glycation reaction, only LR-90 at >1 mM showed significant effect on superoxide produced from this reaction. See FIG. 17B. LR-74, as well as the AGE inhibitor aminoguanidine, had little or no effect on superoxide production.

Example 10

LR Compound Treatment of Diabetic Rats

Diabetes was induced in male Sprague-Dawley rats by a single i.p. injection of STZ (65 mg/kg in citrate buffer, pH 4.5) after an overnight fast. Non-diabetic animals were injected with citrate buffer only. One week after STZ injection, only animals with >20 mmol/L plasma glucose were classified as diabetic and included in the study. Diabetic rats were divided randomly into the following treatment groups: diabetic untreated (D); and two diabetic treatment groups, receiving either LR-9 (D+LR-9) or LR-74 (D+LR-74) at 50 mg/L in drinking water. Three non-diabetic groups were studied concurrently: one untreated non-diabetic group (ND), and two non-diabetic groups treated with either LR-9 (ND+LR-9) or LR-74 (ND+LR-74) at 50 mg/L in drinking water.

Both plasma glucose and body weight were checked before administration of the drug, and no differences were detected among the three diabetic treatment groups or among the three non-diabetic groups. All animals were housed individually and were given free access to food and water. Glycemic control and body weights were monitored periodically. To limit hyperglycemia and ensure that animals maintained body weight, diabetic animals received 3 IU of ultralente insulin two to three times per week. The study was carried out over 32 weeks. Progression of renal dysfunction was assessed by measuring urinary albumin and plasma creatinine concentrations according to known methods. Figarola et al., *Diabetologia* 46:1140-115, 2003.

Diabetic animals had higher glucose and HbAlc concentrations, and lower body weights than non-diabetic rats (P<0.001). Treatment with either L-9 or LR-74 had no effect on hyperglycemia and body weight gains on either ND or D rats. All diabetic animals initially comprised 9 animals in each group. At the end of the study, the numbers were reduced in the diabetic control (n=5), LR-9 (n=6) and LR-74 (n=6)-treated diabetic rats. There was no mortality observed in the non-diabetic groups.

Diabetes was associated with increased urinary albumin excretion and plasma creatinine concentration (P<0.001 vs. non-diabetic control) See Table V. Treatment of diabetic rats with either LR compound inhibited the rise in urinary albumin excretion, with about a 50% reduction in concentration compared to untreated diabetic rats. The elevated plasma creatinine concentrations observed in diabetic animals also were significantly decreased by almost 50% with treatment of either LR-9 or LR-74. Additionally, diabetic rats had higher kidney weights (measured as a fraction of total body weight) compared with non-diabetic animals (P<0.05), indicating renal hypertrophy. Treatment of either LR compounds partially attenuated these changes. See Table V.

TABLE V

Rat Physical and Metabolic Parameters.

| Group | n | Kidney/Body wt. Ratio[a] (g/100 g) | Plasma Creatinine (mg/dl) | Urinary Albumin mg/42 hr) |
|---|---|---|---|---|
| ND | 4 | 0.58 ± 0.02 | 0.45 ± 0.06 | 4.8 ± 0.9 |
| ND + LR-9 | 4 | 0.51 ± 0.01 | 0.42 ± 0.02 | 4.8 ± 1.2 |
| ND + LR-74 | 4 | 0.52 ± 0.01 | 0.42 ± 0.03 | 4.6 ± 1.2 |
| D | 5 | 2.14 ± 0.27* | 3.13 ± 0.38* | 32.8 ± 3.6* |
| D + LR-9 | 6 | 1.58 ± 0.11** | 1.79 ± 0.39** | 18.0 ± 3.7** |
| D + LR-74 | 6 | 1.52 ± 0.10** | 1.64 ± 0.44** | 14.3 ± 3.7*** |

[a]Ratio of left and right kidney weights to body weight.
*P < 0.05 vs. ND;
**P < 0.05 vs. D;
***P < 0.01 vs. D.

Example 11

AGE Immunohistochemical Staining

At 32 weeks of the study, the rats were killed by overanesthetization with isoflourane and cardiac puncture. Blood samples were collected from each animal and transferred accordingly into heparinized vacutainer tubes and were later centrifuged for plasma isolation. Aliquots of these plasma samples were stored at −70° C. until the time of analysis. Kidneys were removed immediately, decapsulated and rinsed in PBS buffer. Sections of the left kidneys were stored in 10% neutral buffered formalin for subsequent microscopic examinations and AGE immunohistochemistry. Sections of abdominal skin and tail of each individual rat were removed, rinsed in PBS buffer and stored at −70° C. for subsequent AGE quantification and crosslinking analyses.

Immunohistochemical staining for AGEs in rat kidney demonstrated that there was widespread staining for CML-AGE in the kidney glomeruli and cortical tubules in diabetic rats compared with the non-diabetic control rats. Treatment with either LR compound clearly protected against the increase in CML-AGE deposited in these regions, primarily in the glomeruli. See FIG. 18.

Example 12

AGE Formation in Collagen

Tail tendon collagen was isolated from each rat in Example 11 and the degree of AGE formation in collagen was assessed by measurement of fluorescent AGE after enzymatic digestion. Figarola et al., *Diabetologia* 46:1140-115, 2003. Skin collagen isolation and reduction was performed as described in Shaw et al., *Methods Mol. Biol.* 186:129-137, 2002. Levels of AGEs/ALEs were normalized to the lysine content of the collagen samples.

Figure 19:
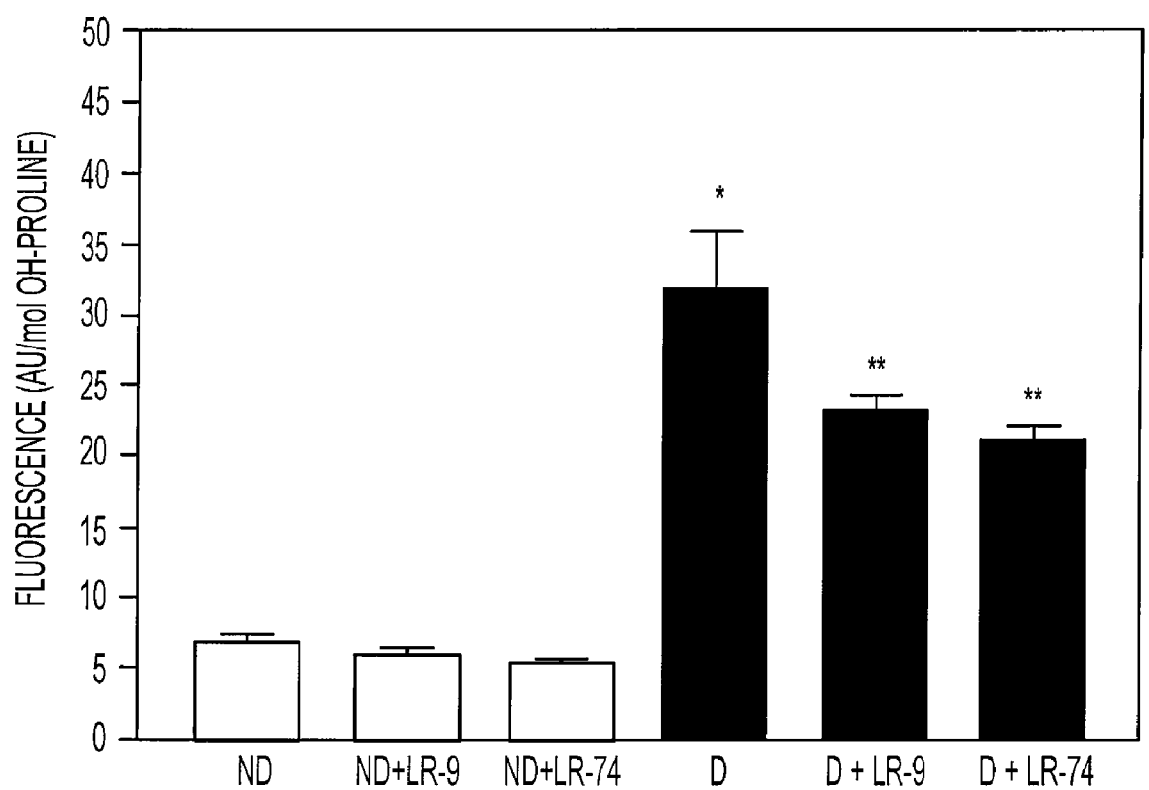
FIG. 19 shows the effects of diabetes and LR treatment on levels of fluorescent AGE in tail tendon collagen. Tail tendon collagen was digested with pepsin and the supernatant analyzed for fluorescent AGE and OH-proline content. (* indicates $p<0.01$ vs. ND, ** indicates $p<0.05$ vs. D).

The levels of fluorescent AGEs in tail collagen increased about five-fold in untreated diabetic rats compared to untreated non-diabetic animals. See FIG. 19.

Ion-pair reversed-phase liquid chromatography/tandem mass spectroscopy analysis was performed using an Agilent Technologies™ LC1100 series system interfaced to a Micromass Quatro™ Ultima Triple Quadripole Mass Spectrometer. HPLC separation was achieved using a Phenomenex Synergi™ Hydro-RP 4 µM 80A 150×2.0 mm column preceded by a Phenomenex C18 guard column. The column temperature was maintained at 25° C. and the flow was 0.2 mL/minute. The isocratic mobile phase consisted of 10% acetonitrile and 0.1% heptafluorobutyric acid in water. Total run time was 12 minutes; injection volume was 20 µL. The autoinjector temperature was 5° C. The electrospray ionization source of the mass spectrophotometer was operated in the positive ion mode with a cone gas flow of 190 L/hour and desolvation gas flow of 550 L/hour. The capillary voltage was set to 2.7 kV. Cone and collision cell voltages were optimized to 25 V and 13 eV for CML, 33 V and 12 eV $d_4$CML, 24 V and 14 eV for CEL, 29 kV and 14 eV for $D_8$CEL, and 29 kV and 16 eV for lysine, respectively. The source temperature was 125° C. The desolvation temperature was increased to 300° C., and the solvent delay program was used from 0 to 3 minutes and 10 to 12 minutes. The fragmentation of these compounds can be induced under collision dissociation conditions and acidic mobile phase. The precursor→product ion combinations at m/z were 205.1→130.11 for CML, 209.12→134.12 for $d_4$CML, 219.11→130.11 for CEL, 227.18→138.16 for $d_8$CEL, 147.15→84.21 for lysine and 151.27→88.33 for DL-$d_4$Lysine were used in multiple reaction monitoring (MRM) mode to determine these compounds. MassLynx™ version 3.5 software was used for data acquisition and processing.

All solutions of standards and internal standards were prepared in water. Standard solution containing both CML and CEL were prepared at six concentrations: 4, 10, 20, 40, 100 and 200 pmol/mL for CML and 2, 5, 10, 20, 50 and 100 pmol/mL for CEL. Quality control solutions were prepared at two concentrations: 7.5 and 150 pmol/mL for CML and 3.75 and 75 pmol/mL for CEL. A stock solution of heavy-labeled internal standards ($d_4$CML and $d_8$CEL) was prepared at 800 pmol/mL. For generation of a standard curve, 130 µL of standard solution was freshly mixed with 10 µL 0.1 M ammonium bicarbonate, 10 µL 0.05% HFBA and 10 µL internal standard stock solution to give a caliber. The calibrators then were assayed in duplicate to establish the standard curves for CML and CEL. The calibration curve was plotted with the ratio of standard peak area to internal standard peak area (Y) against the standard concentration (X). The standard curves, as determined by linear regression, displayed good linearity over the range tested ($r^2$>0.99). For the treatment samples, each sample was further diluted 1:16 with water before mixing with the internal standard solution. Then 130 µL of this diluted sample was freshly mixed with 10 µL 0.1 M ammonium bicarbonate, 10 µL 0.05% HFBA and 10 µL internal standard stock solution.

For lysine content determination, standard solutions of L-lysine were prepared at 5 concentrations: 0.4, 0.8, 1.6, 3.2 and 6.4 nmol/mL. Quality control solutions were prepared at 2 concentrations: 0.6 and 5 nmol. A stock solution of internal standards (DL-$d_4$Lysine) was prepared a 1 µg/mL and for the generation of standard curves, 100 µL of standard solution was freshly mixed with 10 µL 0.05% HFBA and 20 µL internal standard solution to give a calibrator. The calibrators then were assayed in duplicate to establish the standard curves. The calibration curve was plotted with the ratio of standard peak area to internal standard peak area (Y) against the standard concentration (X). The standard curves, as determined by linear regression, displayed good linearity over the range tested ($r^2$>0.99). Each rehydrated collagen sample was further diluted 1:3000 with water before mixing with internal standard solution. Then 100 µL of diluted sample was freshly mixed with 10 µL 0.05% HFBA and 20 µL internal standard stock solution.

Figure 20A:
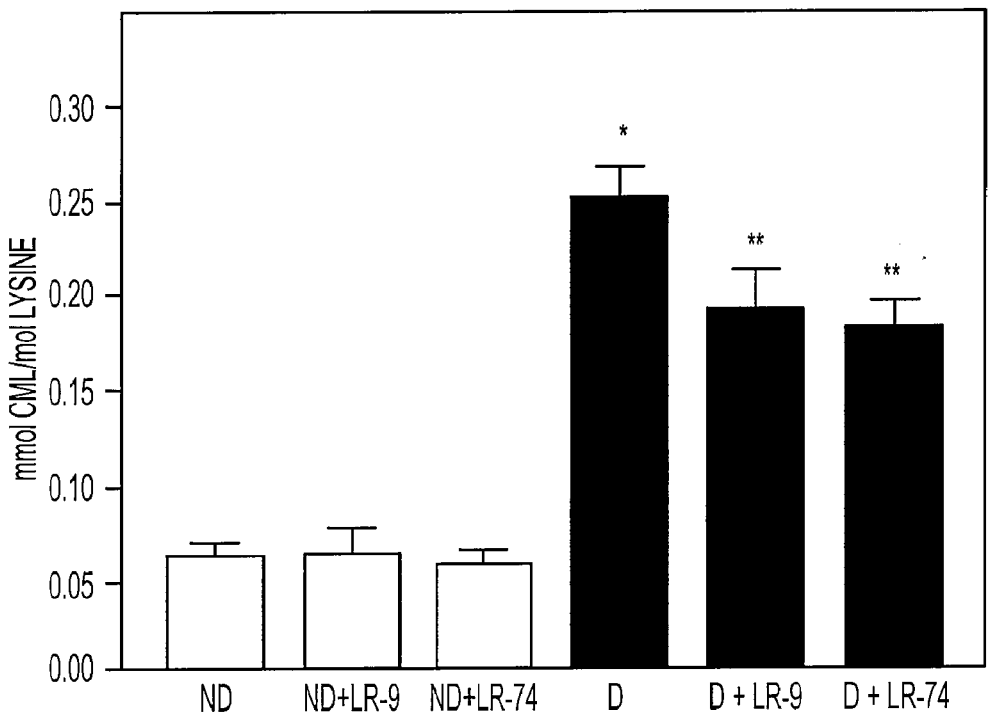
FIG. 20 shows the effects of diabetes and LR treatment on levels of AGEs/ALEs in skin collagen. Skin collagen was analyzed for concentrations of CML (FIG. 20A) and CEL (FIG. 20B) using LC-ESI/MS/MS. * indicates $p<0.01$ vs. ND; ** indicates $p<0.05$ vs. D.
Figure 20B:
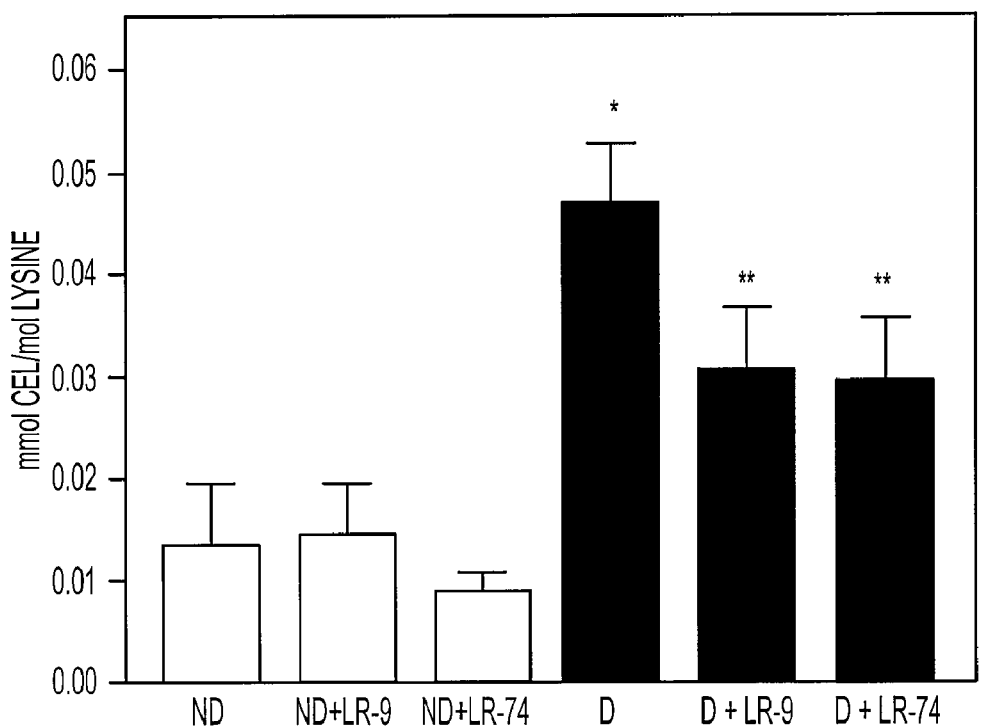

Using the overall LC-ESI/MS/MS technique, the within-day coefficient of variation (CV) was less than 4.1% and less than 5.9% for CML and CEL, respectively. Between day CVs were less than 8.3% for CML and less than 5.6% for CEL. Analysis of the AGE/ALE contents of skin collagen showed significant increase in both CML and CEL concentrations in untreated diabetic animals versus untreated non-diabetic animals. LR-9 and LR-74 treatment significantly limited the increase in both CML and CEL concentrations. See FIG. 20.

Example 13

Plasma Lipids

Figure 21A:
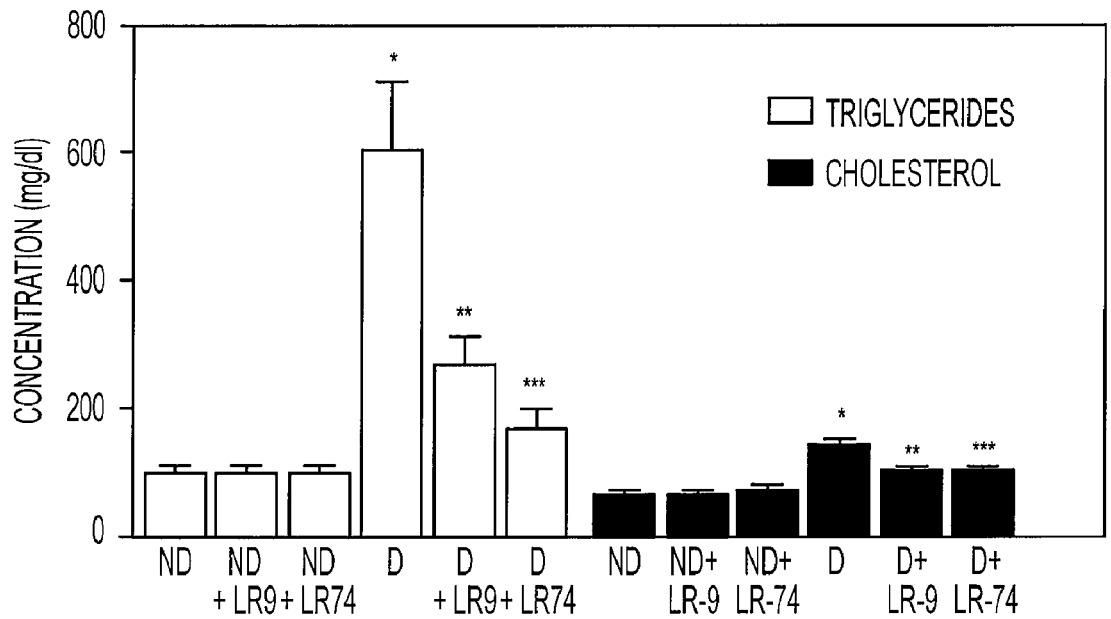
FIG. 21 shows the effects of diabetes and LR treatment on the concentration of (FIG. 21A) plasma lipids and (FIG. 21B) plasma lipid hydroperoxides in STZ-diabetic rats. * indicates $p<0.01$ vs. ND; ** indicates $p<0.05$ vs. D; indicates $p<0.01$ vs. D.
Figure 21B:
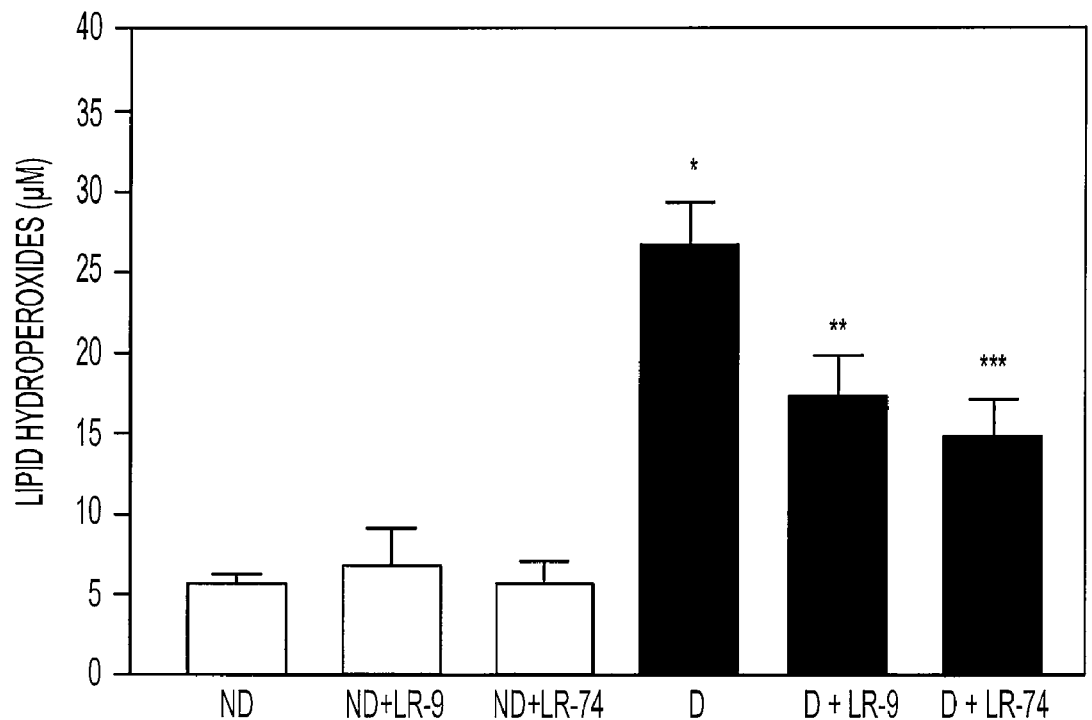

Diabetic rats showed elevated levels of plasma lipids compared with non-diabetic rats. See FIG. 21. Plasma triglycerides increased to 598±110 mg/dL in diabetic rats compared to 86±14 mg/dL in untreated non-diabetic controls (P<0.001). Plasma cholesterol concentrations showed a similar increase in diabetic animals (61±7 mg/dL in non-diabetic vs. 136±13 mg/dL in diabetic rats) (P<0.001). Both compounds had no effect on lipid metabolism in non-diabetic animals. However, diabetic rats treated with either LR compounds showed significant reduction in both triglyceride and cholesterol concentrations. LR-9 reduced plasma triglycerides and cholesterol by as much as 60% and 30%, respectively (means/SEM of 239±50 and 96±5 mg/dL, respectively). LR-74 treatment resulted in almost 70% reduction in plasma triglycerides (161±29 mg/dL) and approximately 30% decrease in cholesterol levels (93±2 mg/dL) compared with untreated diabetic animals. Plasma lipid hydroperoxide concentrations were approximately five times higher in diabetic control rats compared with non-diabetic animals (26.3±2.7 µM vs. 5.6±0.5 µM). See FIG. 21. Treatment with LR-9 or LR-74 substantially reduced plasma lipid hydroperoxides in diabetic animals by 35% and 45%, respectively. See FIG. 21.

Example 14

Effects of LR-9 and LR-74 on Body Weight and Glycemia in STZ-Diabetic Rats

Rats were treated and divided into treatment groups as described in Example 10. Both plasma glucose and body weight were checked before administration of the drug, and no differences were detected among the three diabetic treatment groups or among the three non-diabetic groups. All animals were housed individually and were given free access to food and water. Glycemic control and body weights were monitored periodically. To limit hyperglycemia and ensure that animals maintained body weight, diabetic animals received 3 IU of ultralente insulin two to three times per week. The study was carried out over 32 weeks.

As described above, the diabetic animals had higher glucose and HbA1c concentrations, and lower body weights than non-diabetic rats (P<0.001). Treatment with either L-9 or LR-74 had no effect on hyperglycemia and body weight gains on either ND or D rats. All diabetic animals initially comprised 9 animals in each group. At the end of the study, the numbers were reduced in the diabetic control (n=5), LR-9 (n=6) and LR-74 (n=6) treated diabetic rats. See Table VI. There was no mortality observed in the non-diabetic groups. See Examples 1 and 10.

TABLE VI

Body Weight and Glycemia in STZ-Diabetic Rats.

| Group | n | Body Weight (g) | Plasma Glucose (mmol/l) | HbA1c (%) |
| --- | --- | --- | --- | --- |
| ND[a] | 4 | 668.5 ± 32.8 | 8.5 ± 0.4 | 0.9 ± 0.1 |
| ND + LR-9 | 4 | 681.0 ± 4.6 | 8.2 ± 0.5 | 0.9 ± 0.1 |
| ND + LR-74 | 4 | 744.0 ± 25.8 | 6.8 ± 0.4 | 0.9 ± 0.1 |
| D[a] | 5 | 250.8 ± 19.3* | 26.5 ± 1.0* | 2.1 ± 0.1* |
| D + LR-9 | 6 | 288.0 ± 29.3* | 27.1 ± 0.5* | 2.0 ± 0.1* |
| D + LR-74 | 6 | 314.7 ± 21.6* | 26.9 ± 0.6* | 2.1 ± 0.1* |

[a]ND = non-diabetic; D = diabetic.
*indicates P < 0.05 vs. ND rats.

Example 15

Nitrotyrosine Formation is Increased in Diabetic Rats

Formalin-fixed parafilm embedded kidney sections (2 μm thick) were mounted on slides and stained with polyclonal anti-nitrotyrosine antibodies according to previously known methods. See Figarola et al., *Diabetologia* 46:1140-1152. Nitrotyrosine formation, an index of protein oxidative damage resulting from reactive nitrogen species, was enhanced in diabetic animals, specifically in the proximal tubule cells. See FIG. 22. This increased staining was attenuated by treatment of either LR compound.

Example 16

In vitro Lipid Peroxidation Effects on Human Samples

Human LDL was isolated from plasma of healthy donors by single vertical spin centrifugation (see Chung et al., *Methods Enzymol.* 128:181-209, 1986) and used within 24-48 hours of preparation. LDL (50 μg/mL) was incubated at 37° C. in 50 mM chelex-treated phosphate buffer, pH 7.4, alone or in the presence of 5 μM $CuCl_2$ or 5 μM $CuCl_2$ plus various concentrations of the LR compounds. After 5 hours of incubation, aliquots from each reaction mixture were removed for measurement of thiobarbituric acid-reacting substances (TBARS) as described in Satoh, *Clin. Chim. Acta* 90:37-43, 1978. Briefly, 250 μL of 20% trichloroacetic acid was added to 500 μL of sample aliquot, followed by 750 μL of 1% TBARS. The samples then were vortexed and incubated in a boiling water bath for 10 minutes. Upon cooling, the samples were centrifuged for 5 minutes at 5000 rpm. Absorbance of the supernatant was taken at 532 nm, and expressed as MDA equivalents using 1,1,3,3-tetramethoxypropane as standards. For fatty acid oxidation studies, linoleic acid (5#mM) was incubated alone or in the presence of 1 mM LR compound in 200 nM phosphate buffer, pH 7.4, for 7 days at 37° C. Aliquots from each reaction mixture were withdrawn periodically for measurement of TBARS as described above. Aminoquanidine (AG) and pyridoxamine (PM) were used at 250 μM as comparative controls.

Figure 23A:
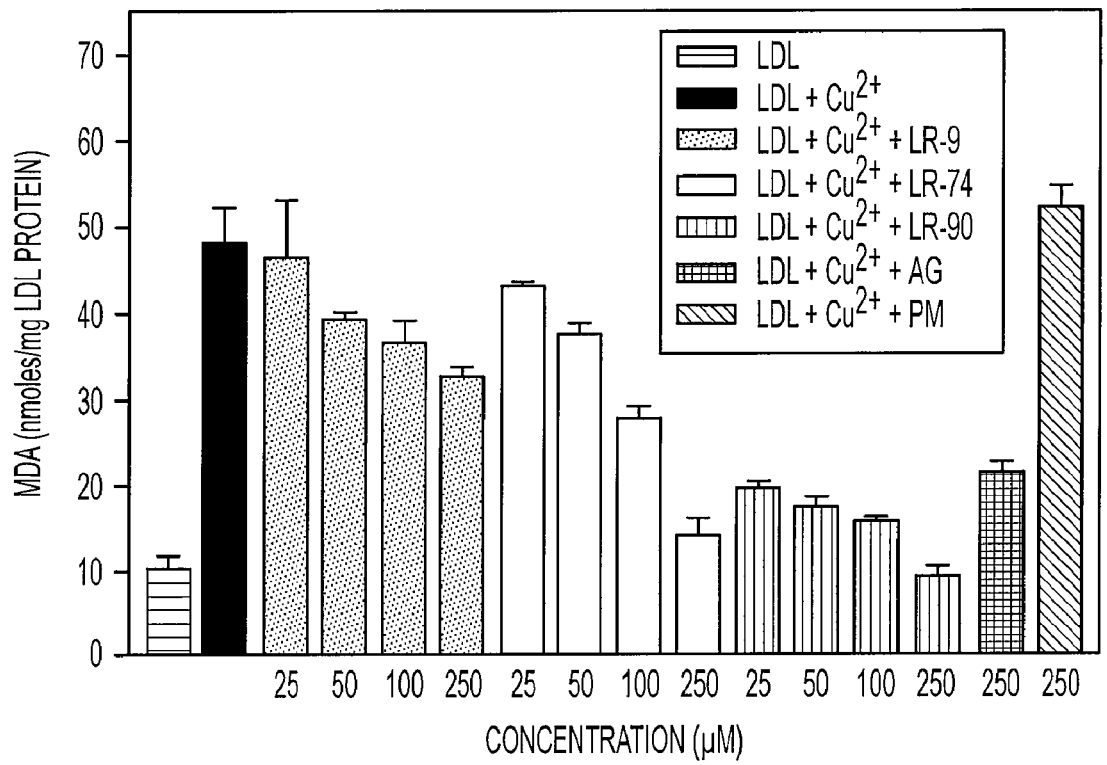
FIG. 23 shows inhibition of $Cu^{++}$-mediated LDL oxidation by LR compounds. Results are shown in FIG. 23A, where values are provided as means±SD of two independent experiments (n=4 for each treatment). Values in FIG. 23B are means±SD of two independent experiments (n=4 per treatment).
Figure 23B:
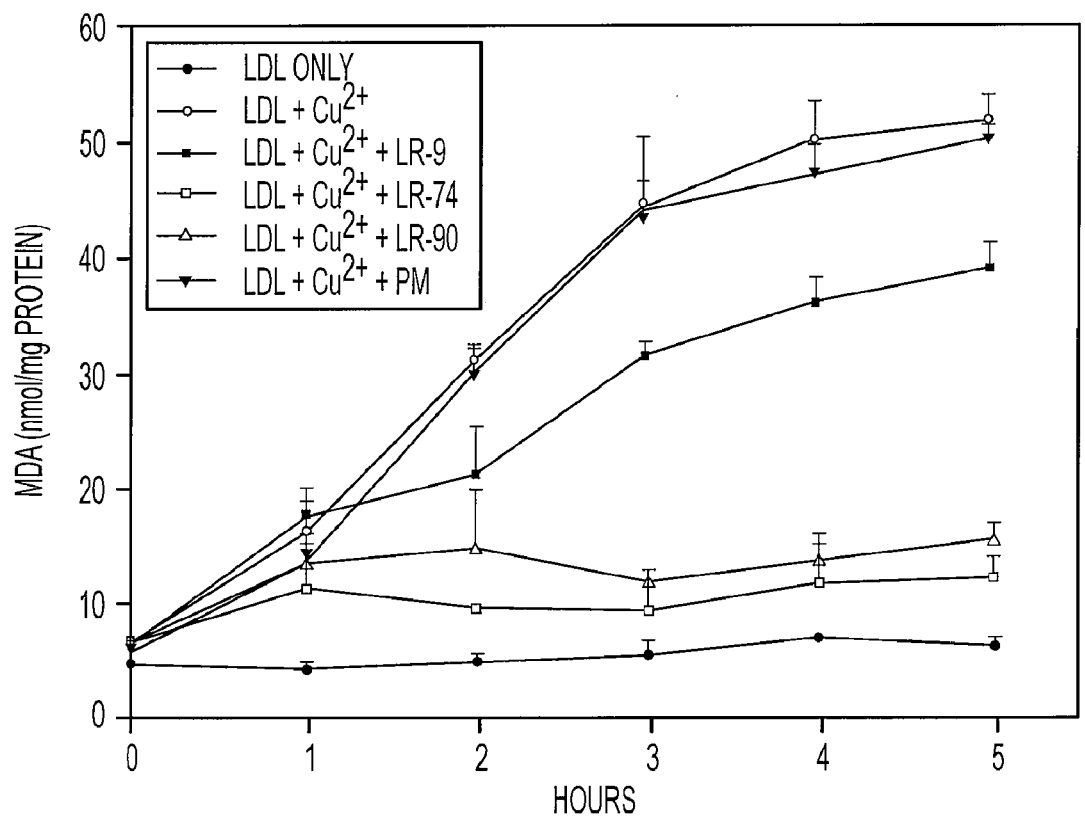

Results are shown in FIG. 23A, where values are provided as means±SD of two independent experiments (n=4 for each treatment). In separate experiments, the time course for the oxidative modification fo LDL by $Cu^{++}$ in the presence of 250 μM compound was followed for 5 hours and aliquots for each time interval were assayed for TBARS. See FIG. 23B. Values in FIG. 23B are means±SD of two independent experiments (n=4 per treatment).

As shown in FIG. 23A, the LR compounds inhibited human low-density lipoprotein (LDL) oxidation in a concentration-dependent manner better than AG and PM. The kinetics of $Cu^{++}$-mediated oxidation of LDL is characterized by two phases, a lag phase of about 2 hours and a propagation phase. The presence of either LR-74 or LR-90 extended the lag phase to such a degree that there was no observable propagation phase. See FIG. 23B. LR-9 significantly inhibited the rate of oxidation after 2 hours compared to the control, while PM had no effect on metal-catalyzed LDL oxidation.

Figure 24:
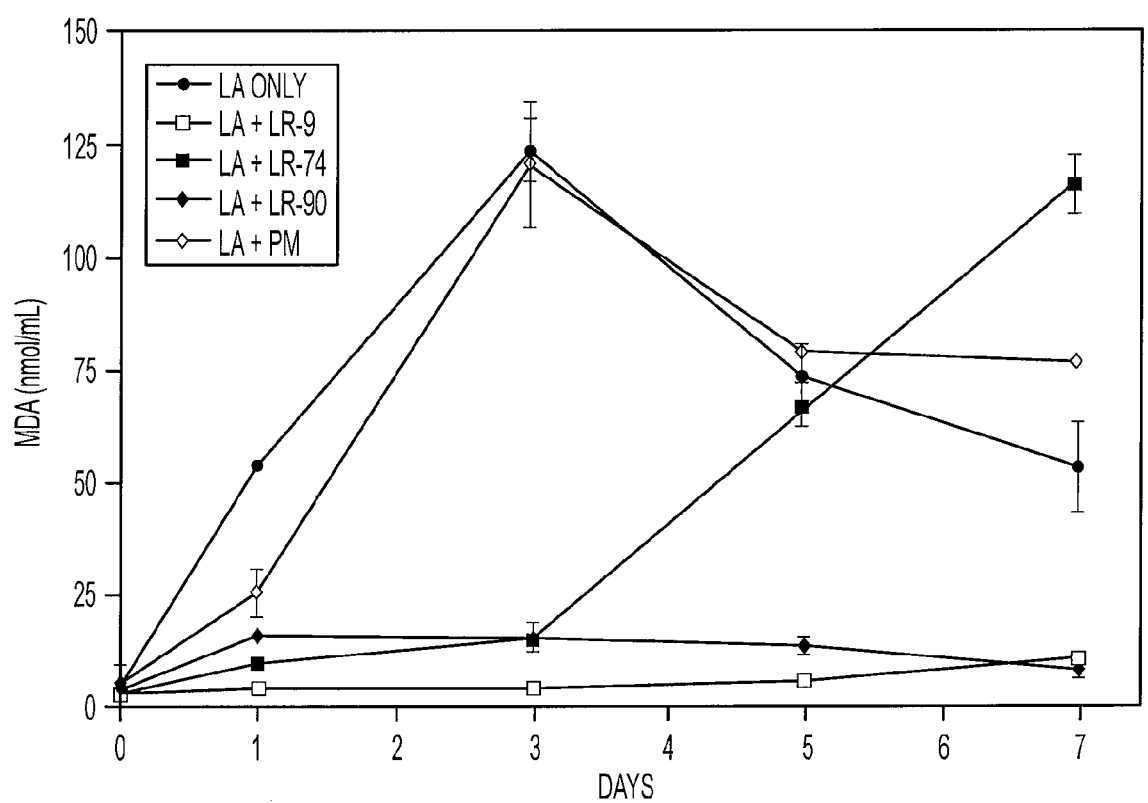
FIG. 24 shows the effects of LR compounds on the kinetics of linoleic acid oxidation. The MDA equivalent was estimated based on standards. Values are means±SD of two independent experiments with n=4 per treatment.

In a kinetic study of the oxidation of linoleic acid (LA), the main fatty acid in LDL, LR compounds prevented the formation of lipid peroxidation products, particularly MDA and related aldehydes. See FIG. 24. Linoleic acid (5 mM) was incubated alone or in the presence of 1 mM LR compound or pyridoxamine (PM), as indicated, in 200 mM phosphate buffer, pH 7.4, for 7 days at 37° C. Aliquots were withdrawn periodically and assayed by the TBARS method as above. The MDA equivalent was estimated based on standards.

LA oxidation increased and reached its peak within 3 days of incubation, then gradually declined after that period. LR-9 and LR-90 totally prevented LA oxidation throughout the 7-day incubation period. LR-74 did not totally prevent the oxidation; it inhibited the maximum oxidation observed at day 3. On the other hand, similar to observations with LDL oxidation, the AGE/ALE inhibitor PM had no effect on LA oxidation. See FIG. 24.

The invention claimed is:

1. A method of lowering lipid levels in a mammal comprising administering an effective amount of a compound or a pharmaceutically acceptable salt of said compound to said mammal wherein said compound is selected from the group consisting of:
   LR-9 [4-(2-napthylcarboxamido) phenoxyisobutyric acid];
   LR-74 [2-(8-quinolinoxy) propionic acid]; and
   LR-90 [methylene bis(4,4'-(2-chlorophenylureidophenoxyisobutyric acid)].

2. The method of claim 1 wherein said compound is LR-9: [4-(2-napthylcarboxamido) phenoxyisobutyric acid].

3. The method of claim 1 wherein said compound is LR-74: [2-(8-quinolinoxy) propionic acid].

4. The method of claim 1 wherein said compound is LR-90: [methylene bis(4,4'-(2-chlorophenylureidophenoxyisobutyric acid)].

5. A method of treating complications resulting from diabetes wherein said complications result from elevated levels of lipids, said method comprising administering an effective amount of a compound or a pharmaceutically acceptable salt of said compound to a mammal wherein said compound is selected from the group consisting of:
- LR-9 [4-(2-napthylcarboxamido) phenoxyisobutyric acid];
- LR-74 [2-(8-quinolinoxy) propionic acid]; and
- LR-90 [methylene bis(4,4'-(2-chlorophenylureidophenoxyisobutyric acid)].

6. The method of claim 5 wherein said compound is LR-9 [4-(2-napthylcarboxamido) phenoxyisobutyric acid].

7. The method of claim 5 wherein said compound is LR-74 [2-(8 quinolinoxypropionic acid].

8. The method of claim 5 wherein said compound is LR-90 [methylene bis(4,4'-(2-chlorophenylureidophenoxyisobutyric acid)].

* * * * *